United States Patent [19]
Massie et al.

[11] Patent Number: 5,636,635
[45] Date of Patent: *Jun. 10, 1997

[54] NON-CONTACT TONOMETER

[75] Inventors: Norbert A. Massie, San Ramon; Bruce W. Maxfield, San Leandro, both of Calif.

[73] Assignee: Massie Research Laboratories, Inc., San Ramon, Calif.

[*] Notice: The term of this patent shall not extend beyond the expiration date of Pat. No. 5,396,888.

[21] Appl. No.: 398,789

[22] Filed: Mar. 6, 1995

Related U.S. Application Data

[63] Continuation-in-part of Ser. No. 775,795, Oct. 10, 1991, abandoned.

[51] Int. Cl.$^6$ .................................................. A61B 3/16
[52] U.S. Cl. ............................ 128/646; 128/649; 128/652
[58] Field of Search ............................ 128/645, 646, 128/647, 649, 652, 664, 665, 661.06, 661.02

[56] References Cited

U.S. PATENT DOCUMENTS

| | | |
|---|---|---|
| 4,951,670 | 8/1990 | Tanaka . |
| 5,148,807 | 9/1992 | Hsu .................................................. 128/645 |
| 5,375,595 | 12/1994 | Sinha et al. ...................................... 128/645 |
| 5,396,888 | 3/1995 | Massie et al. .................................... 128/649 |
| 5,469,848 | 11/1995 | Toleman ........................................... 128/660.02 |

*Primary Examiner*—Angela D. Sykes
*Assistant Examiner*—Samuel G. Gilbert
*Attorney, Agent, or Firm*—John R. Ross

[57] ABSTRACT

A non-contact tonometer is described for measuring the intraocular pressure (IOP) of the eye. An ultrasonic power transducer directs an ultrasonic beam onto the eye and the force generated by the radiation pressure causes indentation or applanation which is detected with an ultrasonic or optical detector. An optical system provides an image of the eye with appropriate alignment beams injected through a beam splitter for positioning the device with respect to the eye. An additional ultrasonic beam may be used to measure the range to the eye. Another optical detector, is utilized to measure applanation or indentation; alternatively, an additional ultrasonic transducer and beam could be used. Operation of the device may be through continuous wave or pulsed excitation of the ultrasound. Feed-back control of the ultrasound power level is possible using an additional ultrasonic transducer for measuring the power levels to augment measurement accuracy.

10 Claims, 19 Drawing Sheets

NON-CONTACT TONOMETER

This is a Continuation-In-Part application of Ser. No. 07/775,795 filed Oct. 10, 1991, now abandoned.

BACKGROUND OF THE INVENTION

1. Field of the Invention

This invention relates to tonometers, devices used for measuring the intraocular pressure (IOP) of an eye, and more specifically to a non-contact type of tonometer which utilizes the radiation pressure of an ultrasonic beam to apply a pressure on the eye and an optical or ultrasonic beam to measure the applanation or indentation caused by the ultrasonic radiation pressure applied.

2. Description of the Prior Art

Glaucoma affects as much as 2% of the population over 40 and is a leading cause of blindness. It damages the eye through increased intraocular pressure (IOP). An ideal means for measuring IOP would be of great value. Unfortunately, current devices for measuring of the IOP, called tonometers, fall far short of the ideal instrument in almost every respect, in spite of the innovative contributions by many workers since the eighteen hundreds.

Over time, various mechanical devices, electronic devices, and most importantly, devices which do not touch the eye have been developed. In spite of intense activity over more than one hundred years, the ideal device has not been previously developed. An ideal tonometer would have several characteristics. First, it should not touch the eye during the measurement; that is, it should be a non-contact tonometer. This avoids the possible transmission of disease between patients, the possibility of corneal scarring, and the risks for adverse patient reaction to the topical anesthetic required for contact tonometry. Second, it should be comfortable to the patient and quiet in operation so as to not startle the patient. Third, it should have an accuracy of at least ±0.5 mmHg over the entire range of IOP's from 10 mmHg to 60 mmHg. Fourth, in use, the results should be insensitive to the technique of the clinician and the measurements should be easy to perform so that tests may be readily performed by clinical assistants. Fifth, the device should be of low cost. Sixth, an ideal device should be amenable to home use. Seventh, the device should be capable of use on patients whether they are supline or erect. Eighth, it should not require periodic recalibration. And ninth, it should be made to be small and hand-held so as to be useful for general practitioners for screening and for use in emergency rooms.

Tonometers presently in use or previously disclosed suffer from a number of shortcomings. One Maklakov developed the impression tonometer in 1885. In this device, a plunger of a known weight is allowed to rest against the eye with the patient in a supline position. The area of contact is determined with a dye, and the weight divided by the area of contact gives the pressure.

An indentation tonometer was subsequently developed by one Schiotz. In this device, a circular foot-plate rests on the eye and a central plunger of fixed weight slides down against the eye. The depth of indentation is indicated by a mechanical lever system and the indentation bears a general inverse relationship to the IOP. However, due to the complex effects of substantial fluid displacement, the IOP must be determined using a complex table. Another disadvantage is that the corneal rigidity and the corneal radius both affect the measurement. Yet another disadvantage of this tonometer is that it is of delicate mechanical construction, requiring great care in use. In spite of the disadvantages of the Schiotz and Maklakov tonometers, they are both used around the world today.

A tonometer having an accuracy greater than that which can be achieved using the Schiotz tonometer was developed in the 1950's by Goldmann (U.S. Pat. No. 3,070,997). In this device, a small biprism is pressed against the cornea. The cornea is prepared by applying a topical anesthetic and a dye which is illuminated by a slit lamp. The image of the glowing tear film around the edge of the prism is split by the biprism such that when just enough pressure is applied to applanate (flatten) the cornea to the diameter of the prism, the half-images of the glowing ring become perfectly aligned. Great skill is required in order to obtain accurate measurements and the disturbances of the intraocular pulse must be averaged out visually. The effects of the attractive force of the surface tension of the tears and the repulsive force due to the bending of the cornea both affect the measurements. For this reason, the diameter of the prism is selected to compensate for these forces on the typical patient as much as possible. In spite of this, the Goldmann tonometer is of questionable accuracy in practice due to problems related to calibration and clinical technique. Also, being a contact tonometer, it can damage the cornea and communicate disease between patients. Finally, it is not easily used by clinical assistants. For the above reasons, it fails to meet the ideal tonometer criteria in most ways. It is, however, sufficiently accurate in the hands of a skilled clinician to be clinically useful for both treatment and screening.

In another contact tonometer, developed by Makay and Marg, a cylindrical and hollow thick-walled tube is contacted to the eye (U.S. Pat. Nos. 3,049,001, 3,150,520, and 3,150,521). A central plunger is then used to measure the restoring force of the eye. This device has also been implemented in a hand-held device about the size of a fountain pen of large bore (U.S. Pat. No. 4,747,296). Measurements with this device are very technique dependent and this tonometer is not widely held to be clinically useful.

In another attempt to develop a better tonometer, in the 1960's, one Grolman developed the air-puff or fluid discharge tonometer (U.S. Pat. No. 3,538,754). In this tonometer, a shod duration puff of air is directed toward the eye. The pressure of this discharge increases with time. When the instantaneous pressure of the air stream at the surface of the eye is equal to the IOP, the cornea is flattened. An optical system detects the moment of applanation, and, by synchronization with the air-puff initiation, can indicate the IOP. This device has not been well accepted by patients since both the noise of generating the air-puff and the sensation of the air against the cornea are objectional. Furthermore, the device is of little clinical value above 30 mmHg due to lack of accuracy. Some versions of the device are so sensitive to clinical technique and alignment that many clinicians cannot obtain results with them at all.

Various other devices have been patented but not utilized commercially. Most follow the lines of the various devices described above. One additional type is the vibration tonometer, first patented in the 1960's (U.S. Pat. Nos. 3,192,765 and 3,882,718). In this device, it is proposed that the response of the eye to a vibrational excitation will be a measure of the IOP. The proposed exciters include very low-frequency sound and mechanical plungers. However, it is likely that the vibrational frequencies of the eye are affected by many factors not related to the IOP. It is, in fact, expected that the actual resonance spectrum of the eye would be dictated more by the connective tissue than by the IOP. All of these factors may be the reason why no commercial use of the vibration tonometer has been disclosed even though its development has been attempted. In addition, the vibration is likely to be very uncomfortable to the patient. There is no known commercial application of this concept in spite of attempts to build a working device.

In summary, no known tonometer meets all of the desired criteria, and none meet the actual clinically preferred level of accuracy and independence of measurements from the clinical technique used. Thus, it is desired to provide an improved non-contact tonometer which meets the above indicated criteria and avoids the shortcomings of the prior art devices as compared to the ideal tonometer.

SUMMARY OF THE INVENTION

In the present invention, the radiation pressure associated with the reflection of an ultrasonic beam from an acoustic impedance mismatch, such as that between the eye and air, is used to indent or applanate (flatten) the eye. A concurrent determination of the ultrasonic radiation pressure and the distortion of the eye allows one to determine the IOP. This technique for non-contact tonometry accomplishes the above objects. First, in contrast to the fluid discharge or air-puff tonometer, the patient does not hear the measurement being conducted. (As described above, operation of the fluid discharge or air-puff tonometers is accompanied by an undesirable sound which tends to startle the patient). The ultrasound frequency for the new radiation pressure tonometer is above human hearing, typically being in the 100 kHz to 1 MHz frequency range. The patient is not likely to feel the force, especially in the embodiment where the pressure is applied slowly and gently in contrast to the fluid discharge tonometers.

The force F associated with the radiation pressure on the eye is given by $F=2 P/v$, where P is the power in the incident ultrasonic beam, and v is its propagation velocity in air. For example, an ultrasonic beam carrying 3.37 watts in air produces a force of 0.02 newtons, which, for a 2 mm diameter beam with a top-hat profile, would generate a pressure of 49 mmHg. Thus, at this level of ultrasonic power, applanation would be achieved for the relatively high IOP of 49 mmHg.

The cornea will reflect all but approximately $10^{-8}$ of the incident power. Thus, for the above example, only 33.7 nanowatts of ultrasonic power would enter the eye. This also corresponds to a power density entering the eye of only 1.1 mw/cm$^2$. Since it is likely that the device will operate in the pulsed mode with at most 0.1 second long pulses, no more than 3.37 nanojoules would enter the eye at a density of 0.1 microjoule/cm$^2$. These numbers are all well below safe and permissible levels.

Since the ultrasound can be focused, applanation spots smaller than that of the air-puff tonometer can be used, further reducing patient sensation to a level likely below the threshold of feeling, in contrast to the fluid discharge, vibration, and Goldmann tonometers. Problems of tear attractive forces associated with the Goldmann tonometer are eliminated. Also, the problems of repulsive forces from bending the cornea should be reduced to a level of no concern, since the ultrasound beams will produce a pressure field with a Gaussian profile, causing only gradual corneal bending. The ultrasound power level can be modulated at high enough frequencies to allow phase-sensitive demodulation for detection of motion of the membranes of the eye. This aids substantially in reducing the sensitivity of the measurement system to many corrupting noise sources. The nature of the ultrasound radiation means that the force is localized and precisely controllable through a standard high-bandwidth servo loop, again in contrast to the use of the fluid discharge or vibration tonometers. Recalibration is not needed as the coefficients of action of the ultrasonic transducers do not change appreciably with time. Such a device may also be compact, portable and hand-held, and thus amenable to home use.

There are additional advantages over the vibration tonometer, regardless of whether the proposed excitation is achieved using mechanical plungers or low-frequency sound. Where low-frequency sound is used as the excitation means, the wavelengths are relatively long (being the order of the diameter of the eye) and cannot be focused on spots which are small compared to the eye diameter. As a result, a very high-intensity sound field is needed. Further, it is difficult to precisely determine the sound intensity at the eye when using an unfocused beam. In the present invention, by contrast, there is no discomforting vibration of the eye. The cornea is not vibrated but gently pushed inwards by the radiation pressure. This completely avoids the enormous difficulty of attempting to measure the complex phase and amplitude response of the biological tissue to low-frequency excitation. Finally, and of very great importance, the results from the ultrasonic applanation non-contact tonometer should follow those of the current clinical standard, the Goldmann tonometer, and thus should closely track a large body of existing clinical knowledge.

The invention will be better understood and other characteristics will appear from the description and the accompanying drawings. The features and advantages described in the specification are not all inclusive, and particularly, many additional features and advantages will be apparent to one of ordinary skill in the art in view of the drawings, specification, and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

DETAILED DESCRIPTION OF THE PREFERRED EMBODIMENT

FIGS. 1 through 9 of the drawings depict various preferred embodiments of the present invention for purposes of illustration only. One skilled in the art will readily recognize from the following discussion that alternative embodiments of the structures and methods illustrated herein may be employed without departing from the principles of the invention described herein.

Figure 1A:
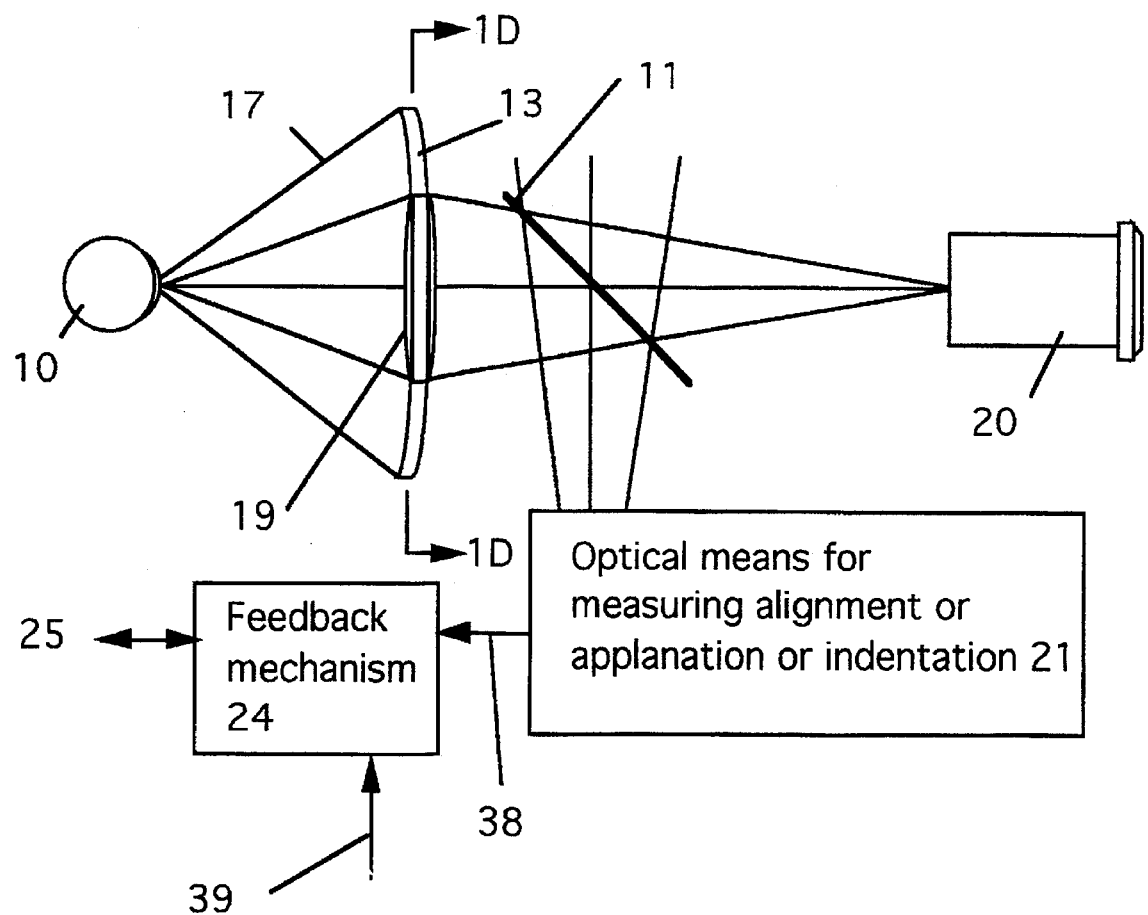
FIG. 1A is a simplified plan view of a non-contact tonometer of the present invention in a coaxial configuration.
Figure 1B:
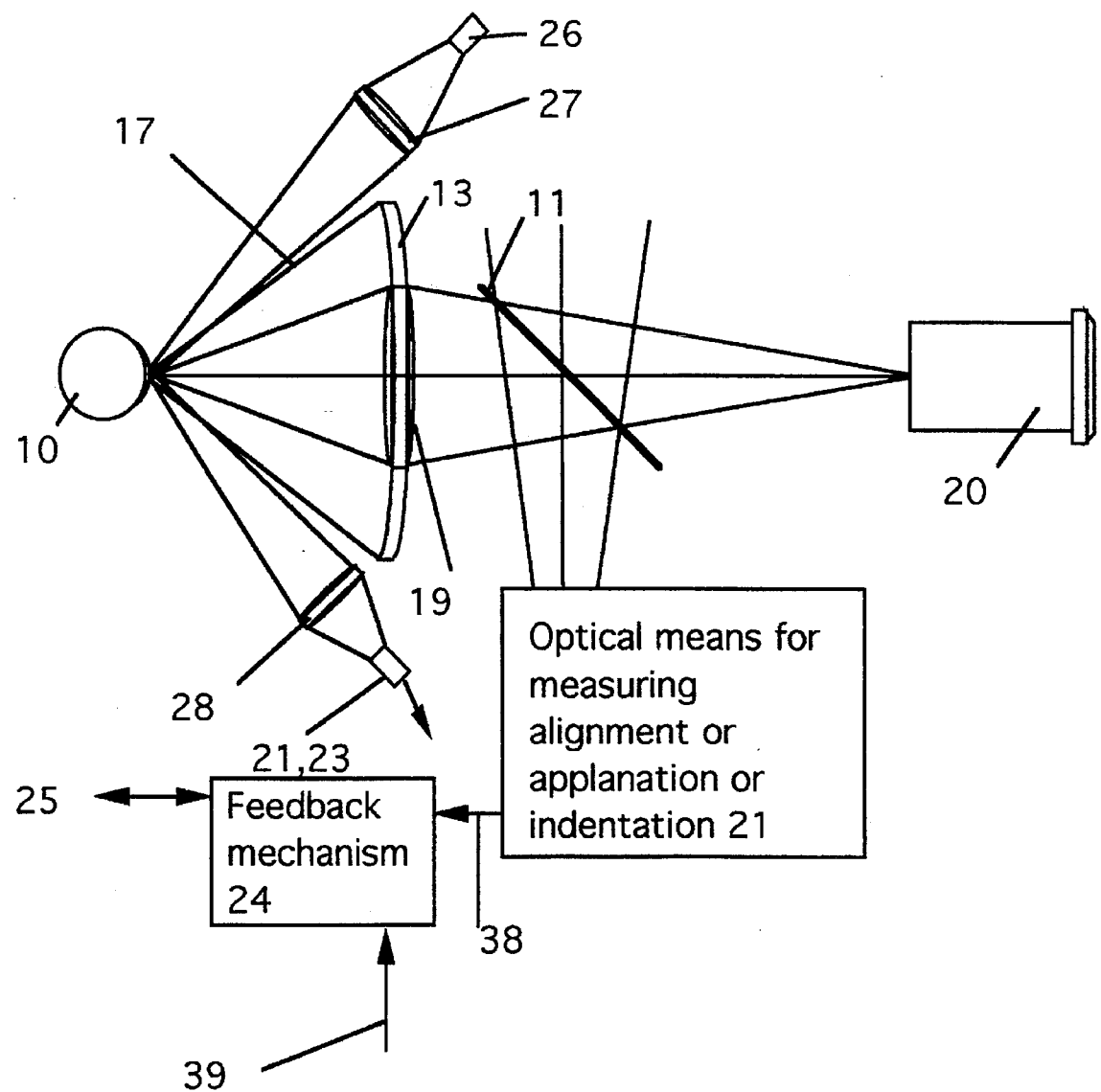
FIG. 1B is a simplified plan view of a non-contact tonometer of the present invention in a side-to-side or side-to-center configuration.
Figure 1C:
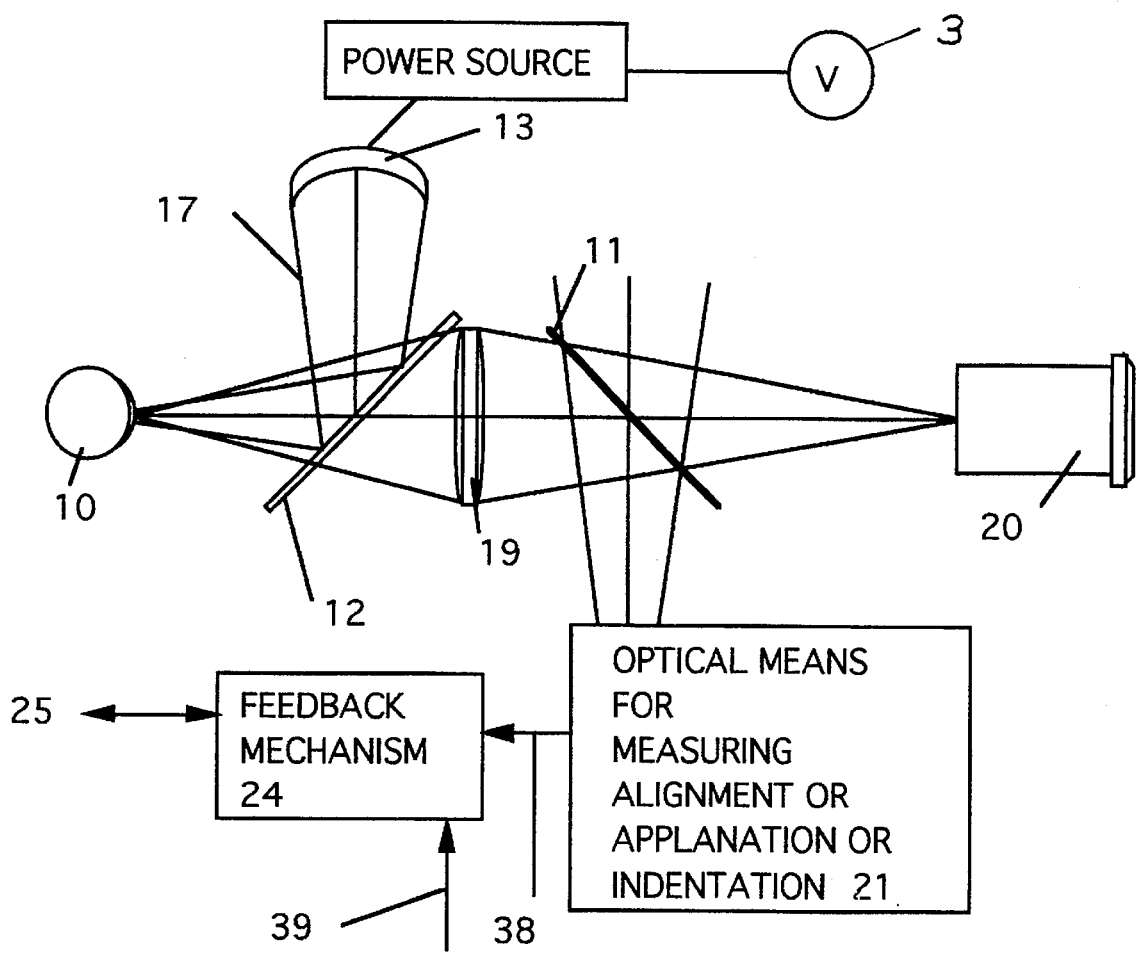
FIG. 1C is a simplified plan view of a non-contact tonometer of the present invention in a reflective configuration.

Specific preferred embodiments of the non-contact tonometer of the present invention are illustrated in FIGS. 1A, 1B and 1C, which are simplified plan views of a tonometer of the present invention in a coaxial configuration, a side-to-side configuration and a reflective configuration, respectively. The term "coaxial configuration" means that the optical and ultrasonic systems have a common axis. Side-to-side or side-to-center means that the sensing beam can be transmitted from the side of the optical system observing the eye and received by either the observing optics or optics on the opposite side of the observing optics.

Similarly, an ultrasonic beam could follow the same path or the ultrasound power transducer could be placed on the side and the sensing beams placed in the middle. For example, FIG. 1B shows a side-to-side optical system. However, all side-to-side systems described could eliminate one side by inserting that side to look through the center by using a beam splitter such as the one shown.

In the reflective configuration illustrated in FIG. 1C, the ultrasonic beam is reflected onto the eye from, for example, a plate of glass which is transparent to the optical system. This greatly facilitates the implementation and packing of the tonometer in some instances.

Figure 1D:
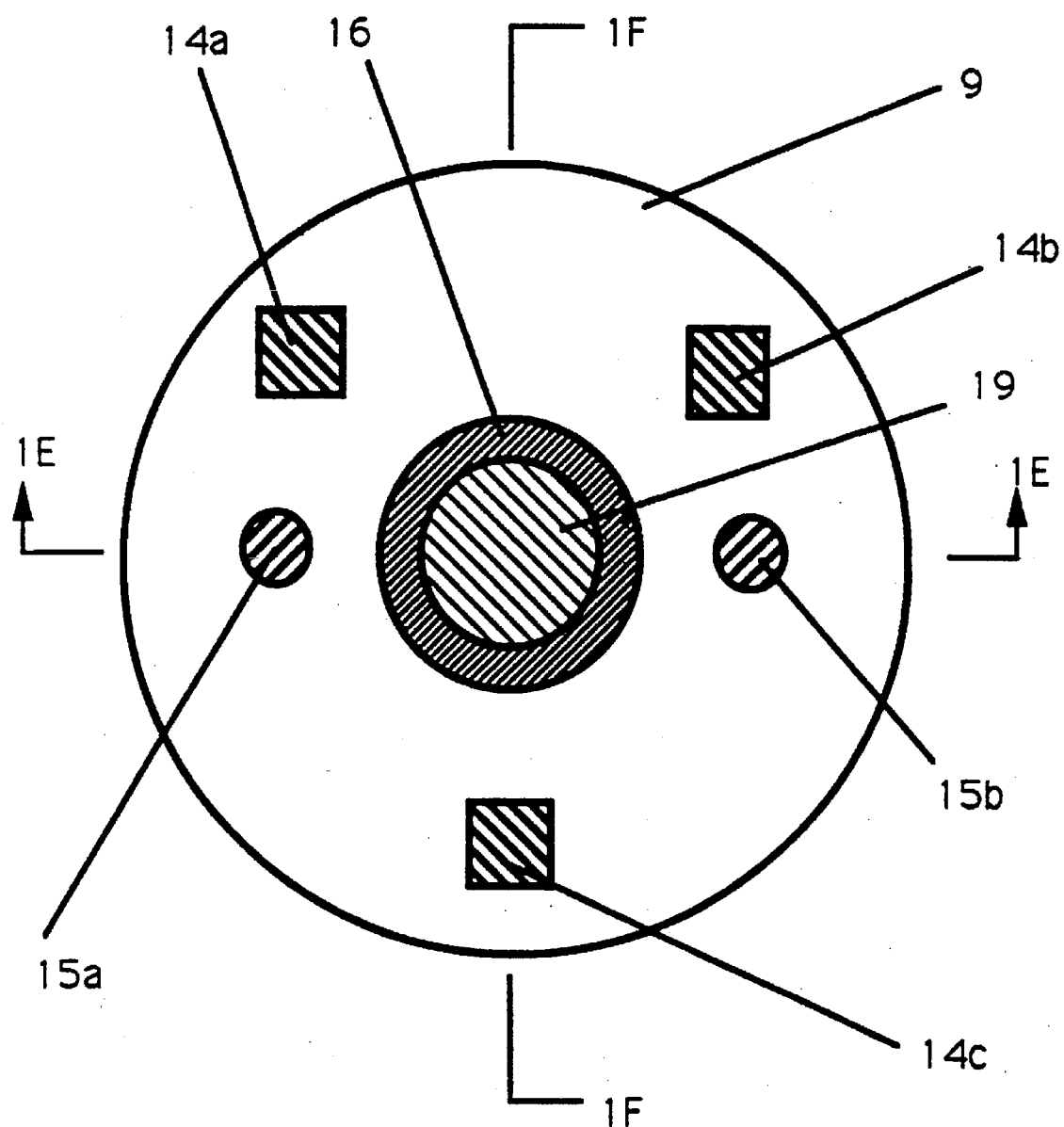
FIG. 1D is a view of an ultrasonic transducer suitable for use in the non-contact tonometer of the present invention taken along line 1D—1D in FIG. 1A.
Figure 1E:
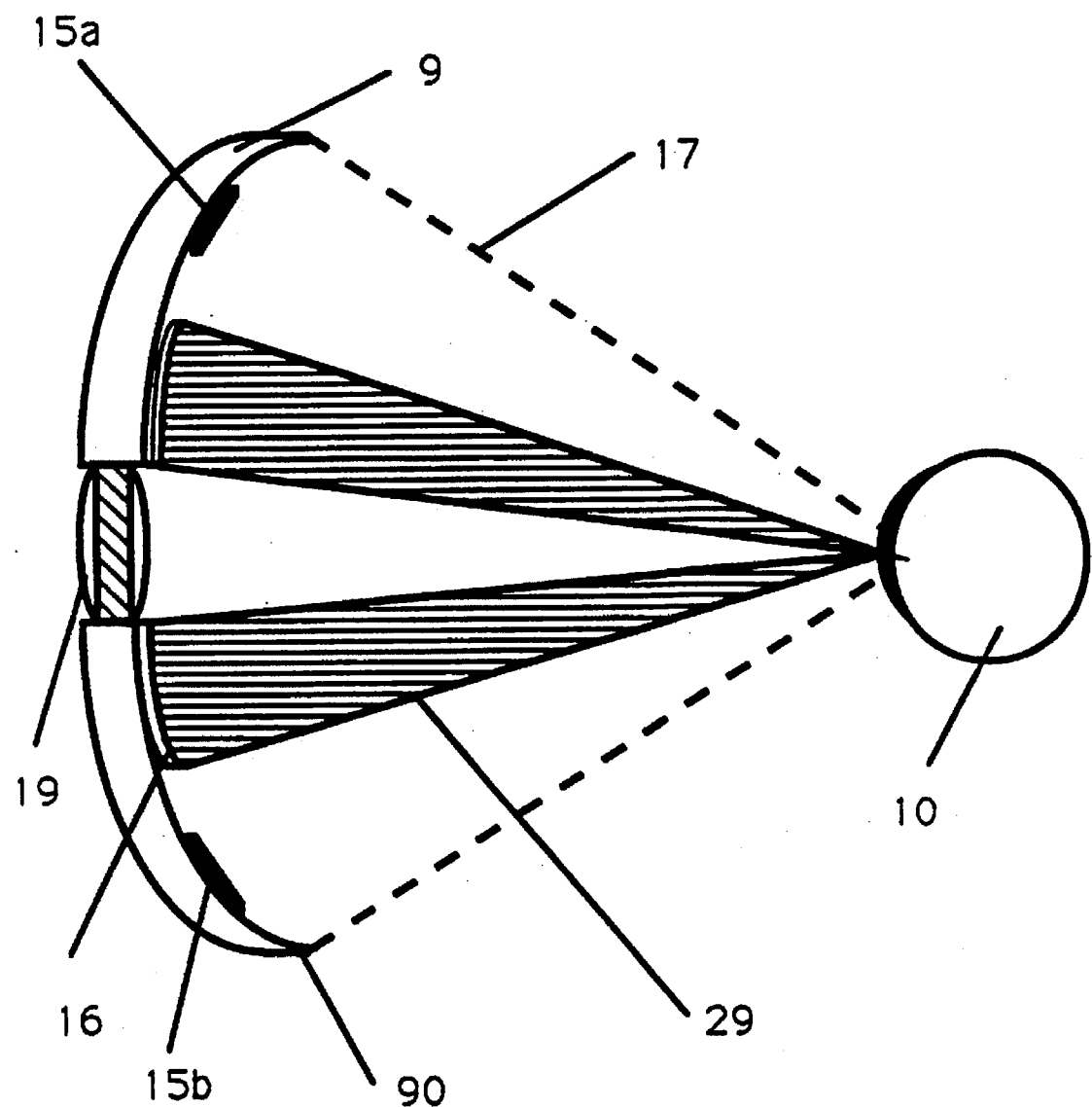
FIGS. 1E and 1F are views of the ultrasonic transducer of FIG. 1D taken along lines 1E—1E and 1F—1F, respectively, in FIG. 1D.
Figure 1F:
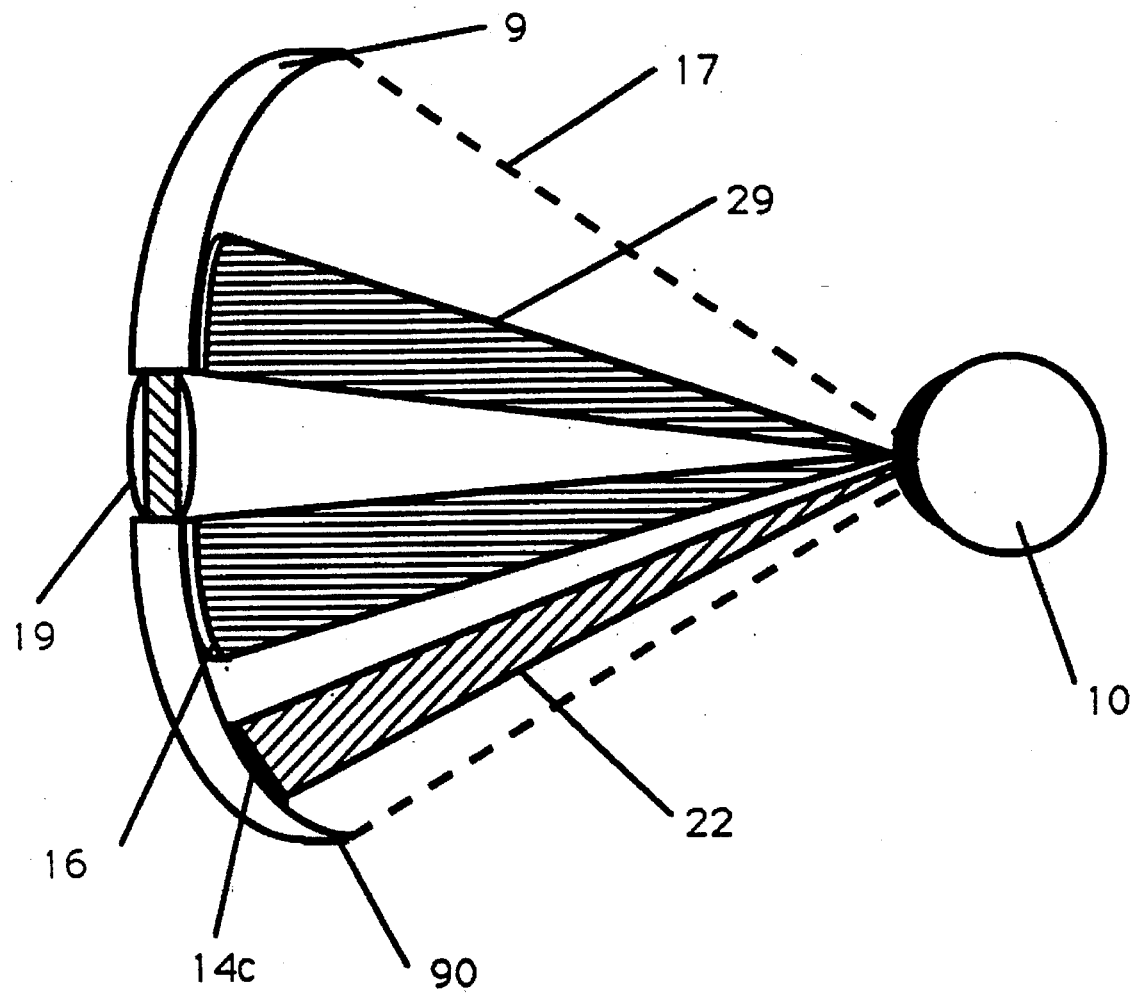
Figure 5A:
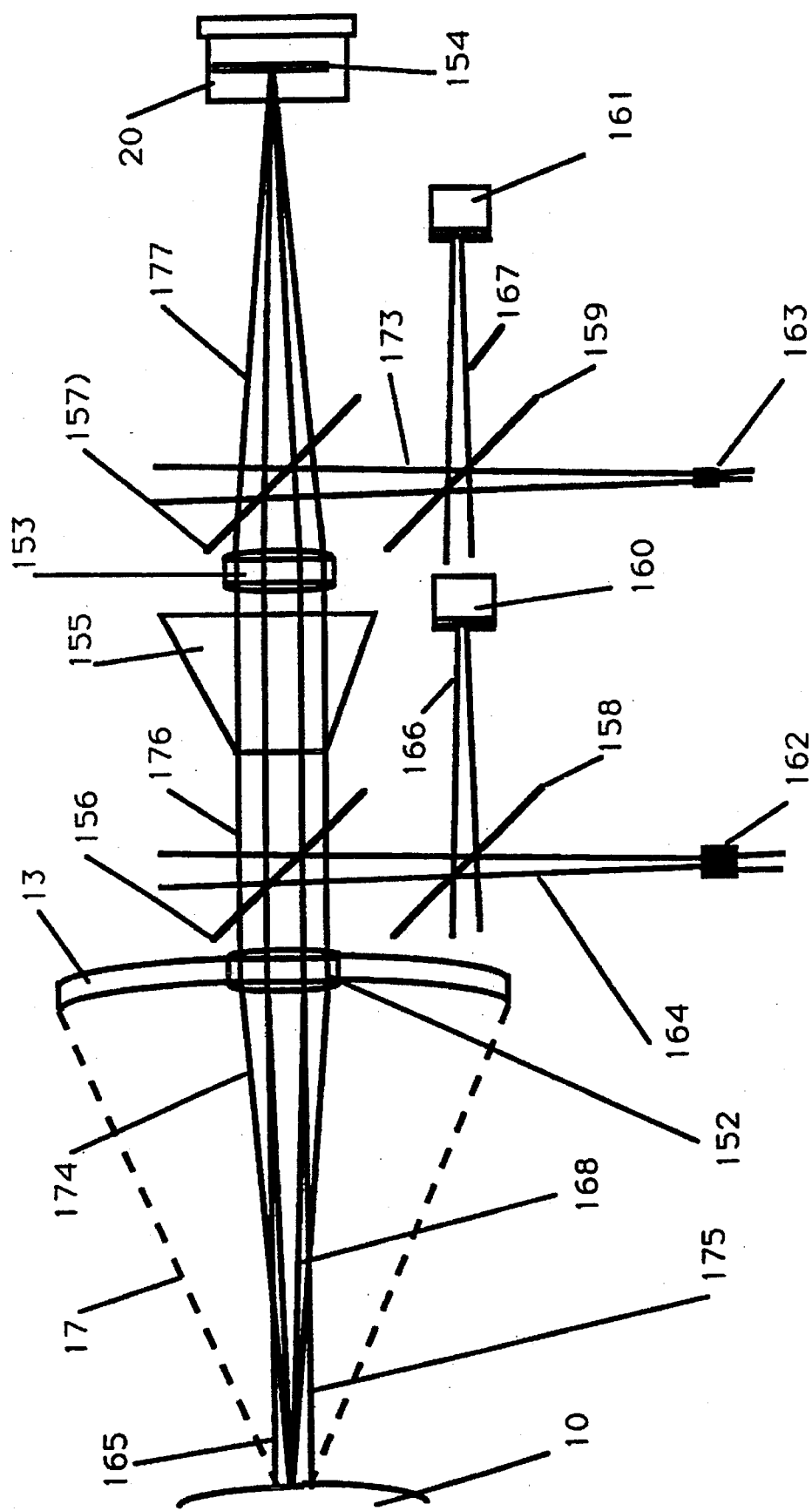
FIG. 5A is a detailed plan view of a tonometer constructed for applanation sensing.
Figure 5B:
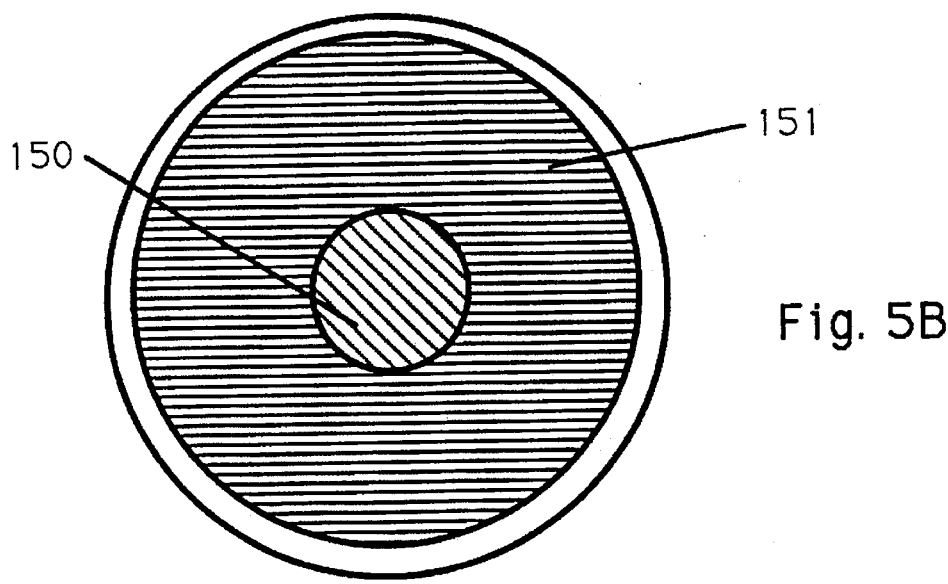
FIG. 5B is a view of an eye as seen through a tonometer eyepiece with no reticles.

Referring to FIG. 1A, a non-contact tonometer is achieved by using the radiation pressure of an ultrasonic beam 17 to indent or applanate the eye and using either an ultrasonic means 16 or an optical means 23 to detect the indentation or applanation of the eye 10. The ultrasound power transducer 13 is oriented so as to direct the ultrasound power beam 17 onto the eye, and the optical system, comprised of objective lens 19 and ocular 20, provides an image of the eye with appropriate optical alignment beams 18 injected through beam splitter 11 for positioning the tonometer with respect to the eye. As shown in FIGS. 1D to 1F, additional ultrasonic transducers 14a and 14b may be used to measure the alignment and distance of the eye using beams 22, augmented by optical means 21 to measure alignment, i.e. the location of the beam on the eye. Optical means 21 may also be utilized for measuring of applanation or indentation although, alternatively, an additional ultrasonic transducer 16 and measuring ultrasonic beam 29 could be used. (FIG. 5A shows optical means 21 as two separate means, one for measuring alignment and one for measuring applanation or indentation.) An additional ultrasonic transducer 15 may be used to measure the power in the cavity formed by the eye and the transducer. Operation of the device may be through continuous wave or pulsed excitation of the ultrasound. Feed-back control of the ultrasound power level is possible using the additional ultrasonic transducer 15 for measuring the power levels and generating power level signal 39, which, along with signal 38 from the applanation or indentation sensor, causes feedback mechanism 24 to generate feed-back control signal 25 to augment measurement accuracy.

FIG. 1D is a view of the front of the ultrasonic power transducer 13, i.e. the side facing the patient. The additional ultrasonic transducers 14, 15 and 16 are shown in suitable locations. Objective lens 19 is located in the center of transducer 13.

As shown in FIG. 1E, ultrasonic transducer 13 is also provided with a special impedance matching layer which allows more power to be coupled into the surrounding medium (typically air). Where ultrasonic transducer 13 is a resonant or quasi-resonant piezoelectric or magnetostrictive element or vibrating diaphragm, the properties of an ideal layer may be calculated using standard laws of acoustic physics. See, for example, Fox, J. D., Khuri-Yakub, B. T. and Kino, G. S., "High Frequency Acoustic Wave Measurements in Air", 1983 IEEE Ultrasonics Symposium, p. 581–84. However, standard materials are not readily available to achieve an ideal match between any of the currently available high power or high displacement piezoceramics and air.

To achieve an adequate matching, layer 90 is made of a silicone rubber, or silicone rubber and a light weight filler, for example glass bubbles or a lightweight filler, mixed with a standard epoxy such as Araldite. Such a composition functions adequately for the purpose of the present invention. The performance of the tonometer is not heavily dependent upon the exact composition and properties of the layer 90, although the closer that ideal matching conditions can be met, the less power must be delivered to and dissipated within the transducer 13. A sufficiently poor match might require an input power great enough to permanently damage transducer 13 or gradually degrade its performance.

The side-to-side or side-to-center configuration of the present invention is illustrated in FIG. 1B. A non-contact tonometer for measuring the IOP is achieved by using the radiation pressure of an ultrasonic beam 17 to indent or applanate the eye and using either ultrasonic means 16 (FIG. 1D) or optical means 21 to detect the indentation or applanation of the eye 10. The ultrasound transducer 13 is oriented so as to direct the ultrasound beam 17 onto the eye and the optical system comprised of objective lens 19 and ocular 20 provides an image of the eye with appropriate alignment beams 18 injected through beam splitter 11 for positioning the device with respect to the eye. Alternatively, the alignment beams may be injected from source 26 and projected through lens 27 and visualized through objective lens 19 and eyepiece 20. The system achieves the same objectives as that shown in FIG. 1A with the main exception that the detection of motion (as opposed to applanation) is now made possible by the non-coaxial injection and reception of optical beams.

The reflective configuration of the present invention is illustrated in FIG. 1C. The ultrasonic power transducer 13 directs a focused ultrasound beam 17 onto the reflective member 12, typically a glass plate. The plate will reflect the ultrasound beam 17 onto the eye 10 but transmit the optical beams which are used for alignment and measurement from the optical objective lens 19. Also shown on FIG. 1C is a voltmeter 3 configured to measure the voltage input to the ultrasonic transducer 13. As above, located with the ultrasound power transducer 13 is an ultrasound power measuring transducer 15 which measures the power circulating in the cavity formed by the eye 10 and the transducer 13. Applanation or indentation may be detected by ultrasound transducer 16 (FIG. 1D) or, alternatively, may be measured by detecting a beam of light reflected from the eye by optical means 21 which would see the eye through beam splitter 11 and objective lens 19. The alignment of the instrument to the eye could be sensed through optical means 21 and/or ultrasonic means 14. As above, feed-back control of the ultrasound power level is possible using an additional ultrasonic transducer 15 for measuring the power levels and generating power level signal 39, which, along with signal 38 from the applanation or indentation sensor, causes feedback mechanism 24 to generate feedback control signal 25 to augment measurement accuracy.

MODES OF OPERATION

1. PHASE SENSITIVE DISCRIMINATION

Figure 2:
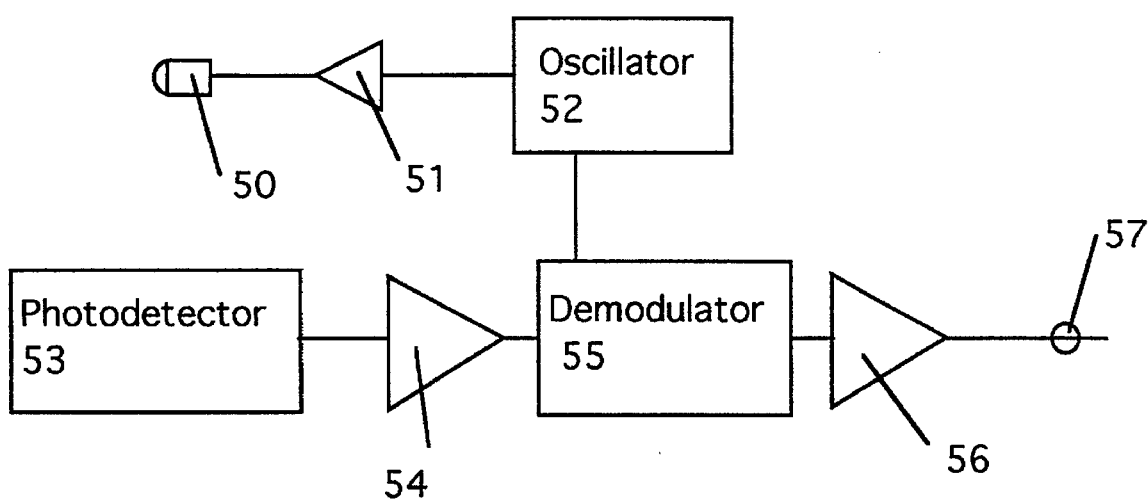
FIG. 2 is a schematic of a circuit for modulation/demodulation of a light source for optical discrimination against room lights and other electrical light sources.

As depicted in FIG. 2, the performance of the system is enhanced by utilizing an encoding scheme on the sensor optical radiation channel. This technique discriminates against room lights, other optical sources, and various sources of electromagnetic interference. Further, since the scheme provides for detection and amplification at frequencies far from DC or line frequencies, the effects of "1/f" noise and line interference are greatly reduced. Referring to FIG. 2, the sensor light source 50 is driven by power amplifier 51 which is fed by oscillator 52 at a frequency f. Thus, the light is modulated at a frequency f and receiving photodetector 53 produces an oscillating signal at frequency f which is amplified by pre-amplifier 54 and fed to phase-sensitive demodulator 55 which obtains its reference signal from oscillator 52. Post-detection amplifier 56 amplifies and band-limits the signal from demodulator 55 and presents it as signal 57. This procedure produces a signal 57 that has a definite and defined relationship to the intensity of the received optical signal and which may be fed to an indicator or to an analog-to-digital convertor for further processing in a digital format. Frequency f is chosen to be relatively high as compared to those contained in room lights or to the line frequency and its harmonics, and also significantly higher than any phenomena that is to be measured. The phase sensitive discriminator discriminates against all signals not in a narrow bandwidth about an appropriate center frequency and not having the correct phase relationship to the reference signal. In this manner, great discrimination and immunity against interfering effects may be achieved.

2. MEASUREMENT BY APPLANATION, INDENTATION OR COMBINATION

Measurement of the intraocular pressure (IOP) using the ultrasonic radiation pressure tonometer may be achieved through one of several basic modes of operation, or through a combination of several modes, herein referred to as the hybrid method. In the applanation or flattening mode, the ultrasonic radiation pressure is gradually increased until the cornea or sclera is just flattened. In the indentation mode, the motion or indentation of the eye is measured for a relatively smaller but preestablished pressure. One example of the hybrid mode is applying both a "steady-state" pressure which is just equal to that required for applanation and a relatively smaller time-varying pressure to modulate motion of the eye about the applanation condition, while measuring the response of the eye to the smaller pressure signal. This hybrid mode may be quite useful for patients with scarred or stiff corneas.

In the applanation tonometer, at applanation, the average ultrasound pressure over the applanated region is just equal to the IOP. This relationship is not affected by the radius-of-curvature (ROC) of the eye. Further, since the pressure field can be made to approximate a Gaussian profile, the pressure tapers off gradually from the center. Thus, the bending of the cornea from flat to curved is slow. The radius of the bending will be substantially larger than that of the Goldmann tonometer where a rigid prism is forced against the eye and the forces of corneal bending must be accounted for in obtaining accurate measurements of the IOP. Another advantage of using applanation is that the detection of the applanation by optical means is easier as compared to the quantitative measurement of indentation.

In the indentation mode, the cornea or sclera is indented by the ultrasonic radiation pressure. The amount of indentation for a given force is a measure of the IOP. This approach has a disadvantage in that the motion is inversely proportional to the ROC of the eye as well as the IOP. Since the ROC varies by nearly 10% in humans, the most accurate absolute measurements can not be obtained without additionally measuring the ROC. While this measurement is commonly performed, it is, nonetheless, a disadvantage to require that it be done. A second disadvantage to measuring the IOP via indentation measurements is that the indentation of the eye may be quite small. Thus, the sensor must be very precise and must also be insensitive to the rather gross motions between the patient's eye and the instrument, making the measurement difficult.

The advantages of the indentation approach are, however, also great. In mass screening programs, it is not the object to obtain the most accurate measurements of IOP but rather to make measurements which are general indications of the actual IOP. It is often more important to make these measurements at minimum cost and with minimum clinical difficulty rather than with the greatest accuracy. Thus, measurement of the ROC may not be necessary. Another advantage is that the ultrasound power level is reduced when compared to the applanation device: this reduces the size and cost of the ultrasound device. Further, the patient's sensation is reduced from that of an applanation measurement. Another substantial advantage is that the ultrasound power level can be amplitude modulated and phase sensitive detection can be used at the sensor, thereby reducing the instrument sensitivity to patient motion.

In the hybrid or combination mode, best advantage may be taken of the special features of various modes of operation. For example, the ultrasonic pressure can be increased until the eye is applanated, or at least, approximately so. Then, a sinusoidal (or other time series) signal can be added to the ultrasonic power, but with an amplitude which is smaller than that required to flatten the eye. The measure of the IOP is then the response of the eye to the smaller signal. An important feature of this approach is that the accuracy of such a technique should be less susceptible to the effects of stiff or damaged corneas and not affected by the ROC of the eye.

3. ALGORITHMS FOR OBTAINING ACCURATE IOP MEASUREMENTS

Figure 3A:
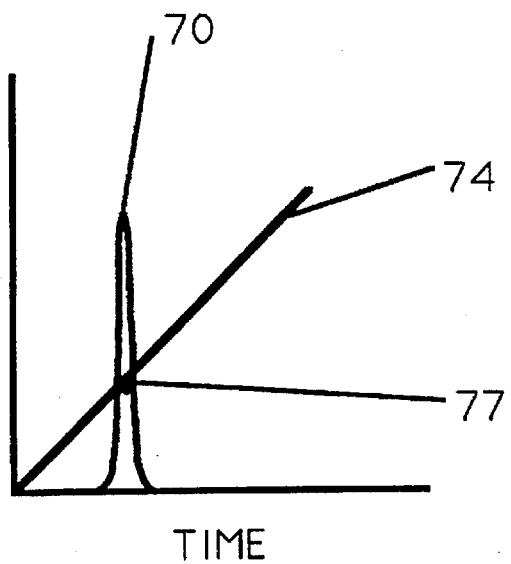
FIG. 3A is a time graph showing the ultrasonic pressure linearly increasing and a resulting applanation spike as seen by the photosensor.

The measurement can be encoded by one of the following schemes. Consider the operation of the tonometer in the applanation mode and the time line for the ultrasonic power and sensor response as shown in FIG. 3A. The sensor for purposes of this discussion is of the type which produces a single peak at applanation.

The ultrasonic power 74 is ramped up over time to a peak pressure level (nominally 60 mmHg). During this time, the sensor output exhibits a very sharp peak 70 indicating the pressure 77 at which applanation occurs. This is the simplest algorithm to measure the IOP. However, more complex schemes may produce more accurate measurements.

Figure 3B:
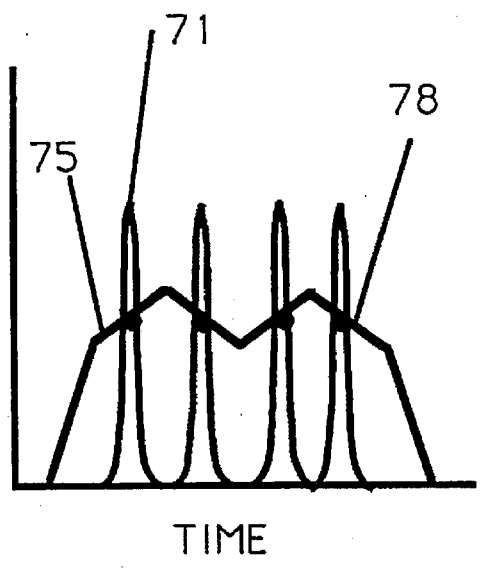
FIG. 3B is a time graph showing the ultrasonic pressure in a sawtooth pattern and resulting applanation spikes as seen by the photosensor.

In FIG. 3B, an algorithm is shown in which, after the applanation peak 71 is reached, the system, possibly under microprocessor control, provides additional ramping of the pressure level 75 such that additional measurements of the IOP 78 can be made using a pressure saw-tooth ramping profile that just brackets the IOP. By this method, an averaging of multiple IOP measurements may be efficiently obtained. This may be important when attempting to discriminate against measurements made during the intraocular pulse where the IOP momentarily surges by as much as 2 mmHg. In one possible processing mode of the multiple measurements technique, measurements not close to the average may be discarded. (The intraocular pulse is only "on" for a small fraction of the time.)

Figure 3C:
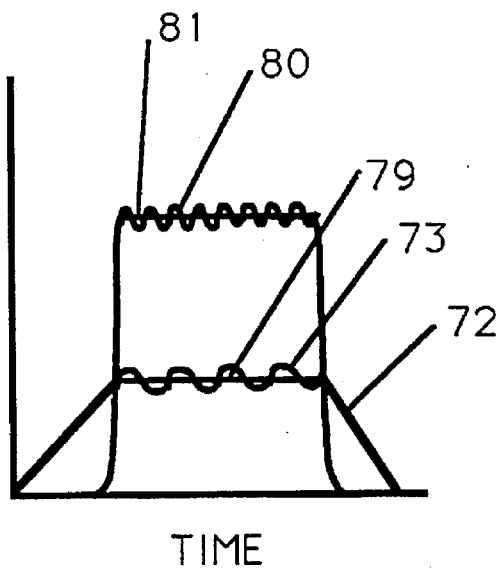
FIG. 3C is a time graph showing the ultrasonic pressure with a small signal modulation and the response of the photosensor.

Another scheme is depicted in FIG. 3C which may be viewed as an implementation of the hybrid IOP measurement technique or as another encoding scheme to improve the measurement accuracy. The ultrasonic radiation pressure 72 is increased until applanation is reached. Thereafter, the pressure follows the form $$A + B \sin(2\pi ft)$$

where f is the power modulation frequency, t is the time, and A (79; FIG. 3C) is the pressure required for applanation and B (73) is much smaller than A. The sensor signal would generally take the form $$C + D \sin(4\pi ft)$$

where C (81) is the photosignal at applanation and D (80) is the component that results primarily from the B $\sin(2\pi ft)$ pressure term. The doubling of the frequency of the photosensor output as compared to the pressure function is due to the bi-directional transfer function of the photosignal at its peak. Proper consideration must also be given to the relative values of the various modulation and/or chopping frequencies that are used in any instrument. If the value of A is too low, the "2 f" signal disappears and the sensor modulation is at f and in phase with the pressure signal. If the value of A is too high, the 2 f signal again disappears but the modulation at frequency f is 180 degrees out of phase with the pressure signal. At the value of A corresponding to the IOP, the value of D would normally be maximized. This signal can be used in a "hill climbing" servo in order to maintain A at the IOP value. Such a system has great advantage in that it can track IOP changes occuring during, for example, a pressure wave caused by the pulse of blood flow to the eye.

APPLANATION TONOMETRY

FIG. 5A shows a more detailed view of a preferred embodiment for an applanation ultrasonic radiation pressure tonometer of the present invention. The sub-systems, to be described separately, include the ultrasound power generation, measuring and ranging transducers, the visualization system which provides an image of the eye for the clinician, the applanation sensor, the patient fixation source, and the transverse alignment indication and detection system.

Figure 5C:
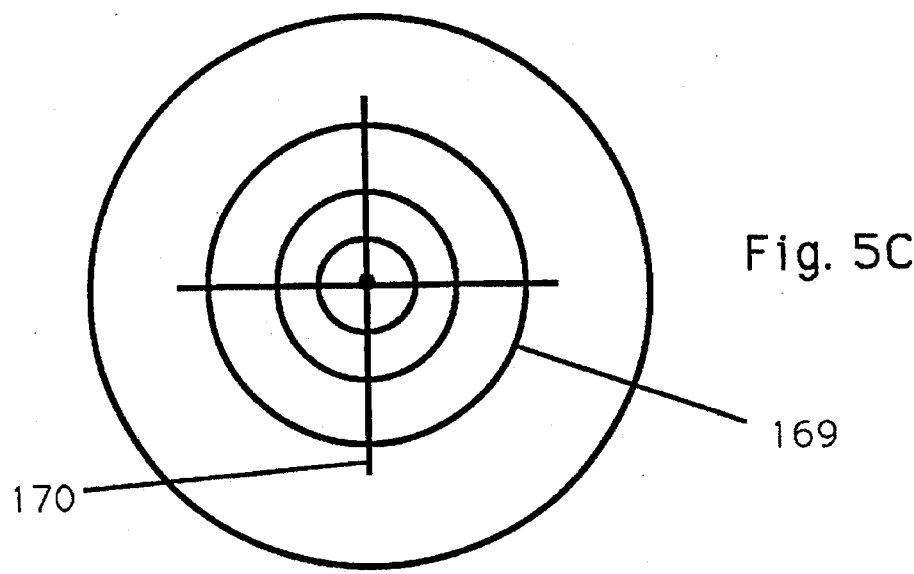
FIG. 5C is a typical reticle pattern.

The eye visualization system is shown in plan view in FIG. 5A. A separate light source, not shown, illuminates the eye. This could be the doctor's slit-lamp, a separate lamp on the tonometer or even the room lights. A first objective lens 152 images the eye 10 to infinity. The light from the eye 174 is collimated into beam 176 in the space between the first objective lens 152 and second objective lens 153. The use of two objective lenses provides a high quality image of the eye 10 at low cost. The space between the objective lenses 152, 153 provides a convenient place to insert the beam splitter 156 that is used for the applanation sensor. Also, the Pecan prism 155 inserted for image erection will not contribute to spherical aberration in this location as it would in a converging beam location such as 177. The second objective lens receives the light from the Pecan prism 155 and refocuses converging beam 177 onto reticle 154. The reticle has a typical pattern as shown in FIG. 5C, and is used as a mark to aid the clinician to align the instrument to the eye. The eyepiece 20 collimates the light for entry into the clinician's eye. In a typical instrument, the image of the eye 10 on the reticle is at a 1-to-1 magnification which also aids in providing an optical system having low aberrations.

Figure 5D:
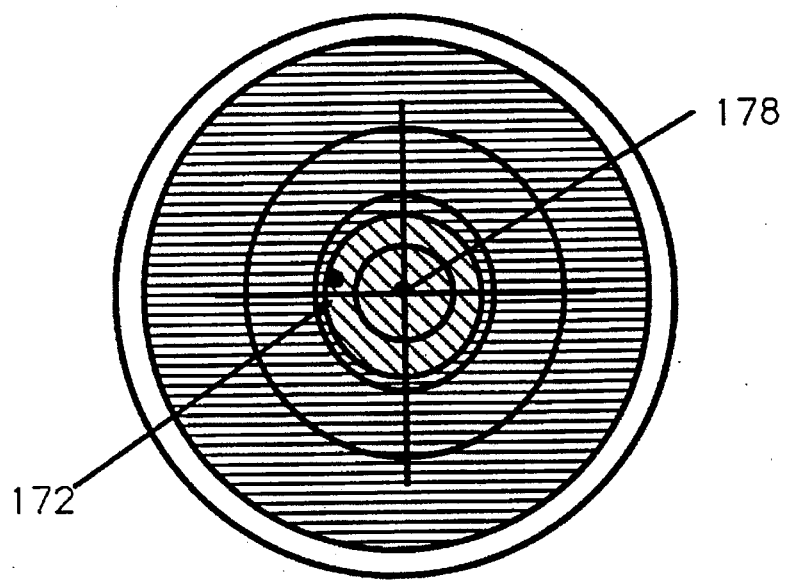
FIG. 5D is a view of an eye, a reticle pattern and alignment beams at misalignment.
Figure 5E:
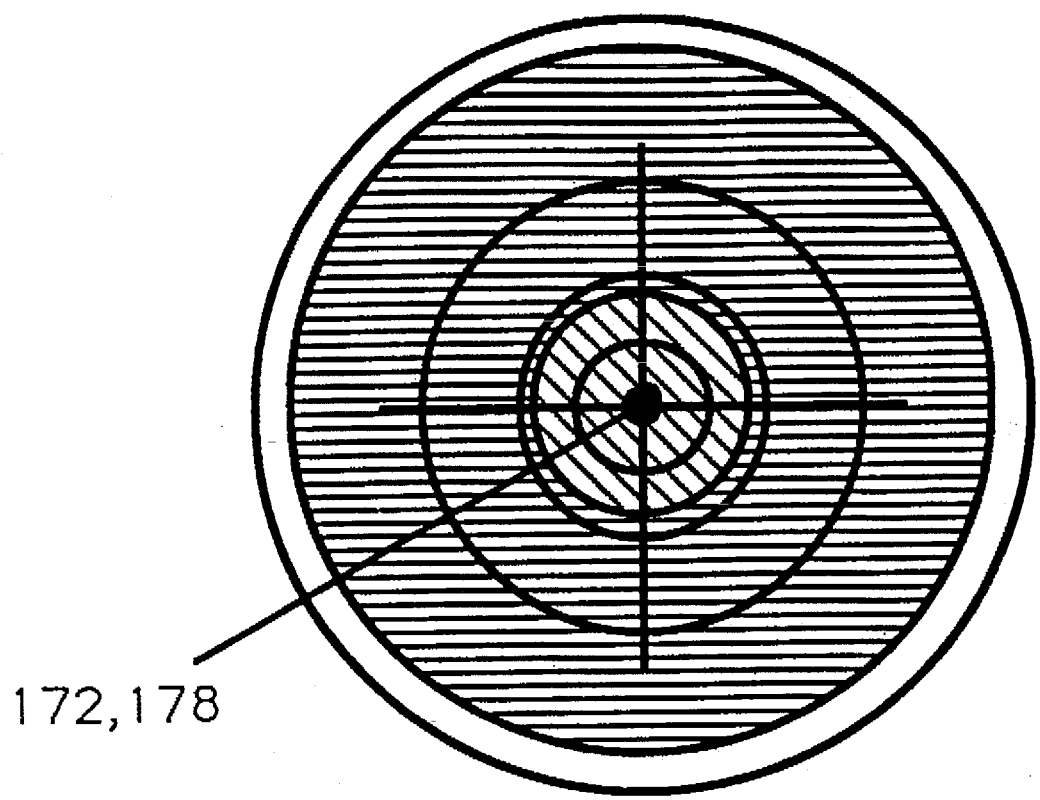
FIG. 5E is a view of an eye, a reticle pattern and alignment beams at alignment.
Figures 5F, 5G:
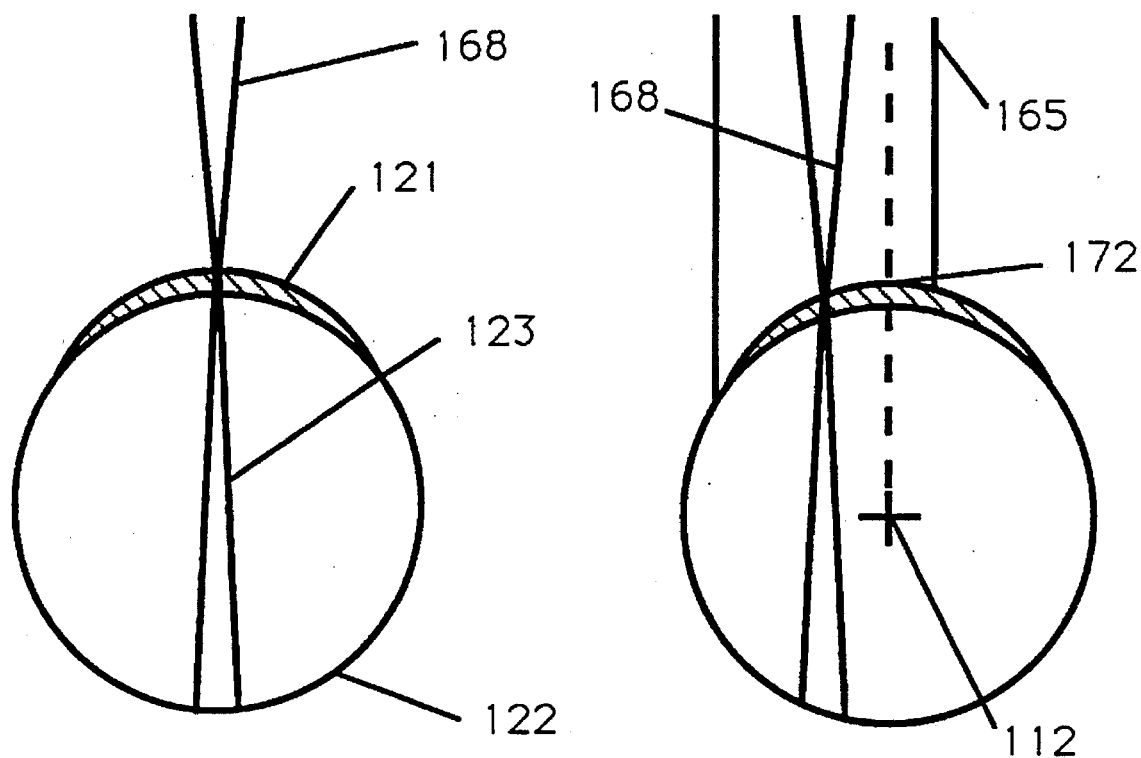
FIG. 5F is a plan view of an eye with an optical fixation beam.
FIG. 5G is a plan view of an eye showing all beams in a state of misalignment.

The patient must be provided with a fixation light source. Preferably, the brightness of this source as perceived by the patient will not be a function of the patient's visual acuity. To accomplish this, a light source 163, here an LED, is provided which is focused at the patient's cornea 121, as shown in FIG. 5F. In this instance, the angular size of the cone of light 123 reaching the patient's retina 122 will be unaffected by the visual error of the patient's eye lens. The radiation from the LED 163 located at the focus of the rear objective lens 153 follows path 173 to be reflected from pellicle beam splitter 157 and into the main optical system. It is collimated into beam 176 in the space between the objective lenses 152, 153 and enters the second objective lens 152. If the instrument is located at the proper distance from the eye (which occurs when the distance between the eye 10 and the front objective lens 152 is equal to the focal length of the lens 152), then the light from LED 163 is focused onto the patient's cornea 121. Since the light has a focus at the eye-lens, the divergence of the light passing through the eye-lens 123 is only slightly affected by the patient's visual acuity. The angle of the cone will, however, be reduced by the index of the medium in the eye. This is important since now the angular extent of the fixation light will be little altered by patients with large refractive errors, which is typical for older persons who are more likely to suffer from glaucoma and hence require tonometry. The LED 163 could, for example, be green to distinguish it from the other LED 162 used elsewhere and described below. Alternatively, it could be flashed on/off in a distinguishing manner from the LED 163. In use, the patient is told to stare at the light from source 163, but in a simplified system, source 162 could be used for fixation alone.

To detect applanation and to align the instrument in the x and y directions and normal to the eye at the apex, light from another light source 162, here also an LED, is used. The light 164 from LED 162 strikes pellicle beam splitter 156 and exits lens 152 as a collimated beam 165. A relaxed eye with perfect refraction for infinity would then see an image of the LED 162. Other eyes will see an out-of-focus image of LED 162. A reflection of LED 162 will be seen at the apex of the eye 172 as located by a plane normal to the optical axis, as shown in FIG. 5G. Through eyepiece 20 the clinician will see this reflection as a glint on the eye; see FIG. 5D. This glint 172 will lie at the point where we desire to focus the ultrasonic beam 17.

Figure 5H:
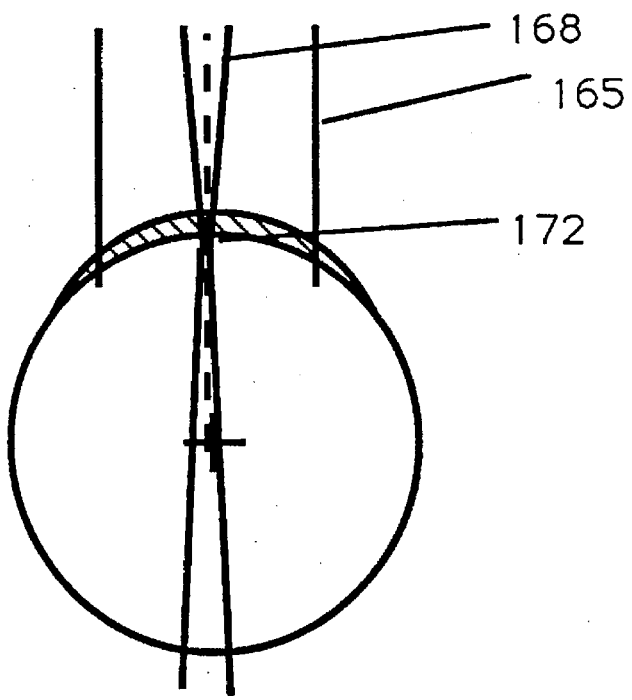
FIG. 5H is a plan view of an eye showing all beams in a state of alignment.

To accomplish alignment, the eye 10 is first visualized. The clinician will see the pupil 150 and the iris 151 (see FIG. 5B) along with the reticle 154 consisting typically of concentric rings 169 and a cross-hair 170 (FIG. 5C). By instrument construction, the reticle is located concentric with the system optical and ultrasonic axes. The image of the eye 10, the reticle 154, and the glint 172 from the collimated beam from LED 162 and the glint from the patient fixation beam 178 is seen as shown in FIG. 5D for a misaligned system and in FIG. 5E for an aligned system. FIGS. 5G and 5H show misaligned and aligned beam positioning from a plan view. Thus, the clinician will be instructed to focus the instrument on the eye and then to move the instrument transversely until the glint 172 is in the center of the reticle 154.

This system indicates motions that are necessary to align the instrument to the eye. To verify that the instrument is aligned transversely, a photosensor 161 is located in the image plane of the eye 10 with its center on the optical axis. Sensor 161 then sees the center of the eye through beam splitter 157. The light that is generated by LED 162 is modulated at a high and known frequency so that sensor 161, with amplifiers being tuned to this frequency, will only produce a valid alignment signal with light from LED 162. Also, an optical passband filter may be located in front of sensor 161 so as to only permit the color of LED 162 to strike sensor 161. When the instrument is aligned in x and y, the signal on photosensor 161 is optimized and the instrument control system indicates to the clinician that alignment is achieved. Only when these conditions are met will the instrument allow the operator to obtain an IOP measurement.

Verification of alignment in the longitudinal direction may be accomplished by an ultrasonic ranging transducer 14. This is a transducer co-located with the ultrasound power transducer 13; its power is also focused on the eye 10. It may also be operated at a lower power and in a shod pulse mode. Since the depth-of-focus of the ultrasound power beam (17) will be several beam waists deep (several mm), the ranging transducer need only have the very modest accuracy of one mm or so, which is quite easy to achieve. To make the instrument even easier to use, the patient-to-instrument distance specification may be relaxed even further and the information from the ranging transducer used to make corrections in calculating the IOP. Also, in a more mechanized instrument, it is possible to incorporate auto-focus and auto-alignment features.

The applanation sensor is now described. The object of this sensor is to detect the moment when the cornea is applanated or flattened. Since the pressure is also known at this time, the IOP can be determined. The LED 162 generates a beam of light 164 which is injected into the optical system through beam splitter 156 and collimated by the front objective lens 152. A flat surface located in the collimated beam 165 and normal to the beam's optical axis would return light to the focal point of front objective lens 152. Thus, photosensor 160, located at the focal point of lens 152, would detect the return beam from a flat surface. If the reflective surface were curved, such as the eye 10 is when not applanated, then the focal spot of the return beam would lie close to infinity and the signal at the photosensor 160 would be inconsequential. The magnitude of the signal at photosensor 160 is thus a very sensitive indicator of flatness of the cornea, and very small changes in the radius of the cornea from flatness can be indicated. Since the system is aligned to the corneal apex and since the force vector of the ultrasound radiation pressure field is parallel to the optical axis, the signal would return ideally to the photosensor 160.

INDENTATION TONOMETRY

The side-to side or side-to-center configuration of FIG. 1B, may be used for an indentation tonometer. The visualization system consisting of objective lens 19 and inverting eyepiece 20 forms an image of the eye onto reticle 154 embedded in eyepiece 20. The side-to-side sensing system is comprised of light source 26, projecting lens 27, receiving lens 28, and motion sensing means 23. Various means to accomplish sensing motion of the eye 10 as caused by the ultrasonic radiation pressure generated by transducer 13 (which produces generating beam 17) are now described.

The light source may be selected from the group of sources consisting of LED's, tungsten-halogen bulbs, etc. and, in one approach, the light is focused by lens 27 onto the eye 10. Lens 28 re-images the spot of light on the eye from either specular or diffuse reflections. The re-imaged spot falls onto a motion sensing device 23. Thus, if the eye 10 is caused to move in the direction of the optical axis of the visualization system by ultrasonic radiation pressure, the optical spot as imaged by lens 28 will move in the direction perpendicular to the optical axis of lens 28, but with a motion modified by the particular chosen geometry. The image of the spot of light on the sensing mechanism 23 will move as well. Thus, the output of the motion sensor will be linearly proportional to the indentation of the cornea which in turn is proportional to the ultrasonic radiation pressure and inversely proportional to the IOP. Various motion sensors may be used. A key feature of the motion sensor will be the ability to detect motions of the spot on the order of I micron caused by the indentation forces from the tonometer at low signal-to-noise ratios (SNR) and in the presence of large scale motions of the eye caused by gross motion of the eye and head.

Figure 6:
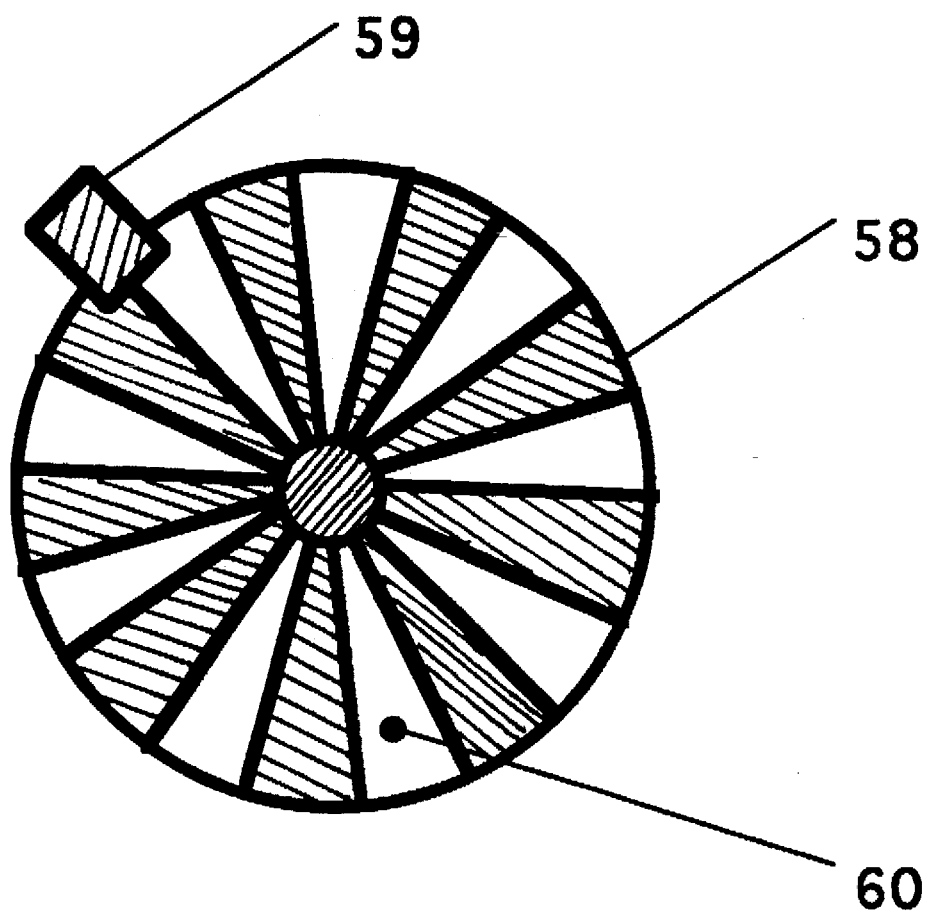
FIG. 6 is a potential pattern for a chopping wheel showing an encoder and an optical spot.

Referring to FIG. 6, motion of the imaged spot may be detected by using a chopper wheel. The wheel as depicted is rotated at a high speed. A photosensor of large area is placed behind the wheel to collect the light regardless of the exact location of the spot 60. The blades of the spinning wheel 58 then chop the light so that the photosensor detects an AC signal. The phase of the signal is determined by the location of the spot with respect to the chopper blades, and the reference phase is detected by the encoding mechanism 59. Thus, the relative phase of the AC signal indicates the location of the spot, and the position sensitivity of the system is approximately the width of the blades divided by the SNR. The dynamic range is in the simplest system the width of the blades. However, by using a simple phase continuation technique, the dynamic range can be extended to nearly the radius of the wheel. By this fashion, the sensor can be induced to have a large dynamic range.

Figure 7:
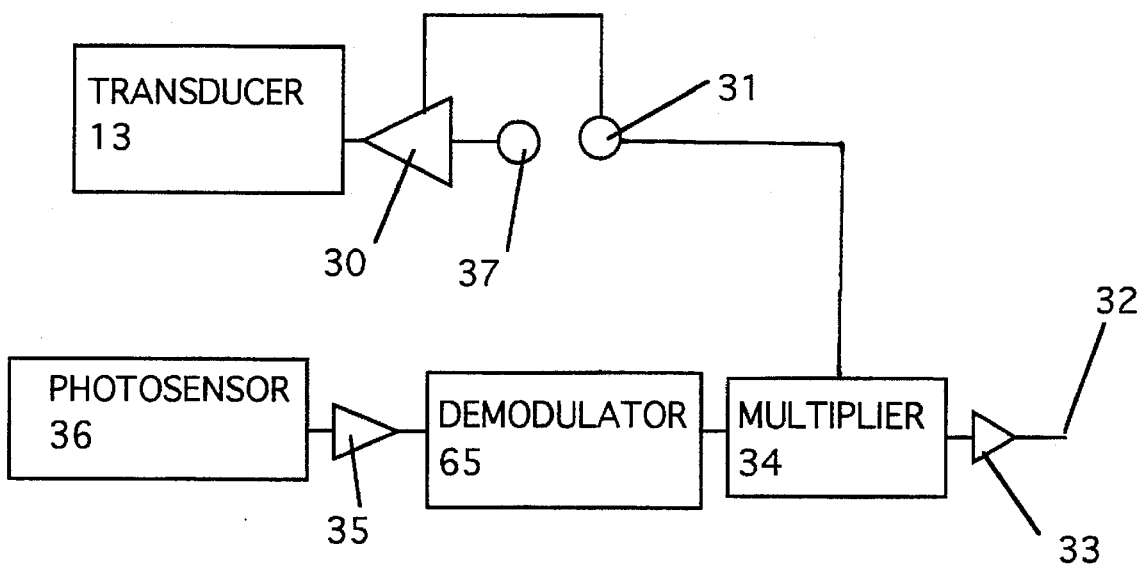
FIG. 7 is a functional layout for an encoding system for optical detection of indentation.

To discriminate between motion of the patient's head (and therefore eye) and eye motions as caused by the ultrasonic radiation pressure, the encoding scheme depicted in FIG. 7 could be used, in addition to, and at frequencies outside, those used for the optical discrimination scheme used against room lights as described in FIG. 2.

As seen in FIG. 7, the ultrasonic power transducer 13 is driven by power amplifier 30, fed by oscillator 37 operating at the desired ultrasonic frequency. Oscillator 31 operates at a convenient audio frequency low enough for the eye 10 to respond with an acceptably small phase lag. Oscillator 31 is used to produce an amplitude modulation of the ultrasonic power output signal. Photosensor 36 receives the light with some modulation encoding the position of the light spot 60. This optical beam modulation is decoded by demodulator 65. The system is designed so that the output of the demodulator 65 is proportional to the motion of the eye 10 and contains information on the patient's head and eye motion and the motion driven by the ultrasonic radiation pressure as well. The radiation pressure induced motion occurs at the frequency of the oscillator 31, however, and the multiplier 34 driven by the reference signal also from oscillator 31 discriminates against all motions not occuring at the frequency of the oscillator 31. The post-discrimination amplifier and band-limiter 33 then produces an output signal 32 proportional to the indentation of the eye 10 caused by a fixed ultrasonic radiation pressure.

Other motion sensors could also be devised. For example, the chopper wheel 60 could be replaced by a linear effect photodiode, or a single photosensor could be used but with a neutral density filter with a linear gradient. In such cases, the spatial resolution would be approximately the linear extent of the device divided by the signal to noise ratio (SNR). In all these concepts, the side receiving device could be replaced with a system looking through the central axis using a beam splitter.

For detection of applanation by the side-to-side system, the peakfocusing system of FIG. 5A could be placed so that it looks onto the eye 10 from the side.

Figure 8:
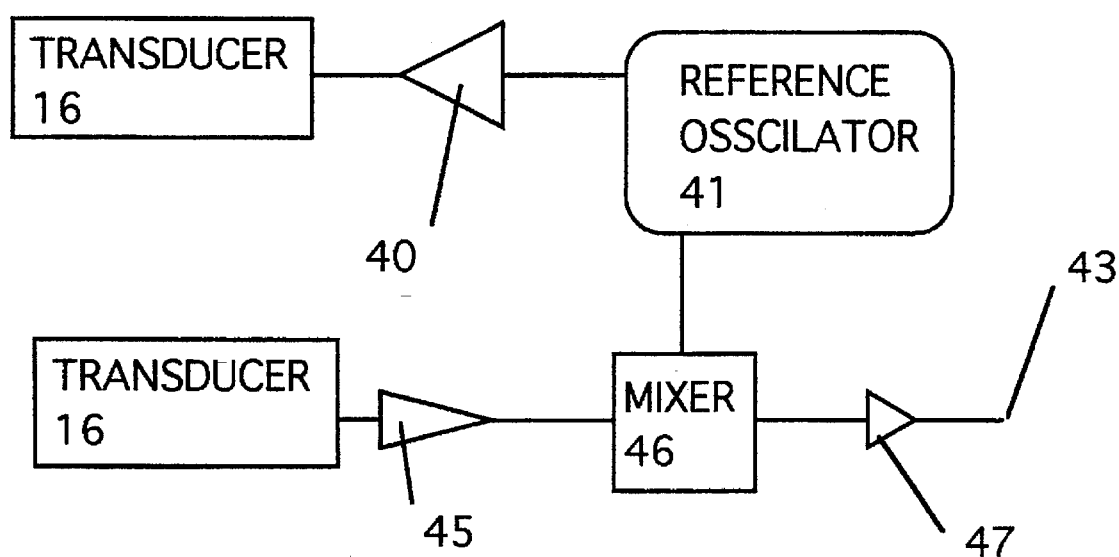
FIG. 8 is a functional layout for an encoding system for ultrasonic detection of indentation.

An indentation tonometer may also be built using high frequency ultrasound to measure the indentation, as illustrated in FIG. 8. Optical means could still be used for alignment and visualization, but the measurement of the indentation would be accomplished by use of separate ultrasound transducers 16 and indentation measurement beams 29. For example, in an indentation tonometer generating enough force to indent an eye 10 by 10 microns, if the transducer 16 is operated at a frequency of 3.37 MHz, then the ultrasound wavelength is 100 microns.

The oscillator 41 drives power amplifier 40 and transducer 16. Transducer 16 is switched from a transmit mode to a receive mode and its output is amplified by amplifier 45. Mixer 46 mixes the output of the reference oscillator 41 with the output received from amplifier 45. The phase difference is amplified by amplifier 47, which outputs a signal 43. The phase difference multiplied by the ultrasonic wavelength and divided by 2 gives the corneal motion.

In this instance, phase detection is used to measure distance, and the accuracy is the ultrasonic wavelength divided by the receiver SNR. For typical installations, this could give a resolution of better than 0.1 micron. A system similar to that of FIG. 7 could be used to discriminate against motions of the patient's head and eye 10 that are not caused by ultrasonic radiation pressure.

In still another embodiment, advantage may be taken of the fact that the ultrasound radiation pressure field produces a nearly pure radius change of the central portion of the eye and that this radius change produces substantial changes in the location of the focal spot of the returned light. The pressure pattern generated by the transducer may be approximated by a Gaussian profile, so that the beam radius (½ of the waist) at focus is approximately $$1.2 \, g \, f/d$$

where f is the focal length, d is the diameter of the transducer and g is the ultrasonic wavelength. In the central region, a Gaussian function can be expanded to first order as a constant minus a quadratic term. The curvature of the eye in this region can also be approximated by a quadratic term. Thus, the deformation, which is proportional to the pressure, is a quadratic variation superimposed on a quadratic function; this is another quadratic function. Therefore, to first order, the effect of the ultrasonic radiation pressure field is to change the radius of curvature (ROC) of the eye.

By using equations describing the relationship between the focal length of a mirror and the distance s to the source and focal spot (for the instance where the distance between the lens and the eye is approximately the focal length of the lens or when the optical source is located at the focal length of the lens), the relative change in the distance to the focal spot of the returning light is given by $$Ws = 4z(f/r_o)2$$

where z is the depth of curvature of the eye from the apex at radius $r_o$, the boundary of the beam waist (i.e., the beam waist has a diameter of $2r_o$). For typical numbers of f=10 cm and $r_o$=1 mm, Ws/z=4 cm/micron. This gives an enormous advantage over measuring z directly. The value of z of a typical deformed eye at applanation is 60 microns so the required resolution for a high accuracy measurement is 0.6 microns. While this accuracy can be achieved, it is difficult because both the patient's head and eye are constantly moving. By this technique, one need only measure the absolute location of the focal spot to within centimeters. The change in distance between patient and instrument enters only in first order, and the ratio is approximately one-to-one. Thus, if the patient can hold still to within 0.5 cm, which is relatively easy, the focal spot motion caused by the ROC change will be much larger. Further, as disclosed elsewhere, the indentation can be encoded so as to discriminate against the unwanted patient motions.

Figure 9:
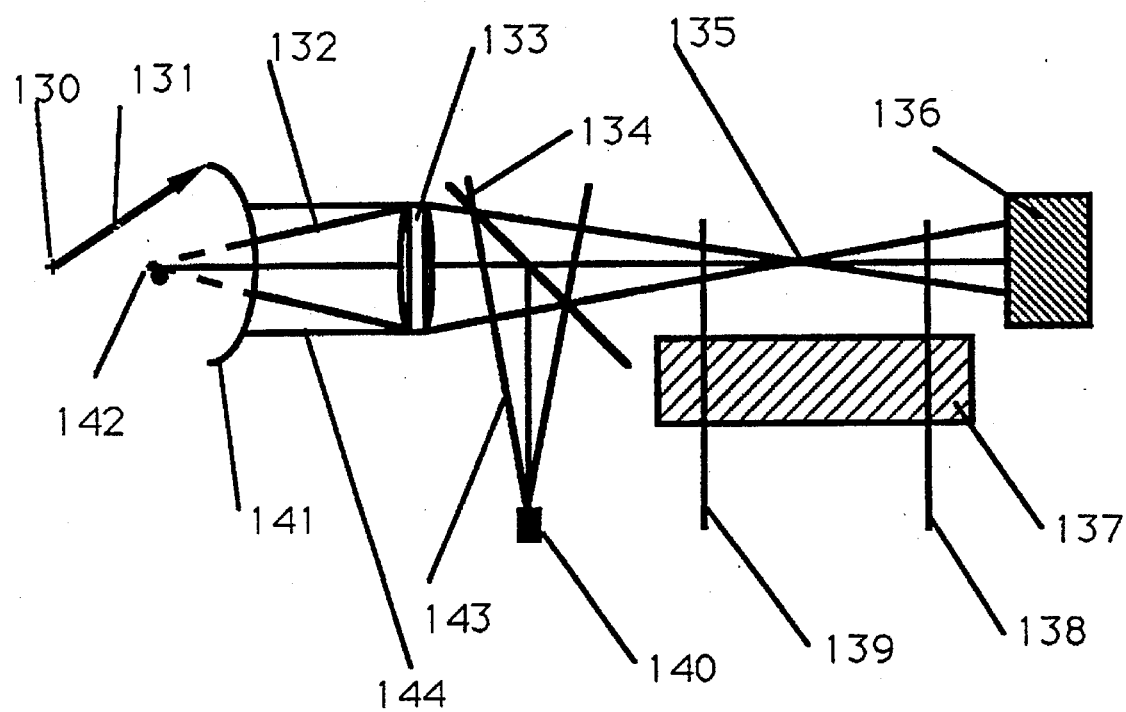
FIG. 9 is a plan view of a tonometer for radius of curvature sensing for indentation detection.

FIG. 9 shows an embodiment of the technique described above. Light source 140 located at the focus of objective lens 133 directs its rays 143 onto beam splitter 134 which in turn directs the light to objective lens 133 where the collimated beam 144 strikes the cornea 141. The reflected light 132 appears to emanate from virtual source 142 located at one-half the distance to the center of curvature 130 of the eye of radius 131. The returned light comes to a focus at location 135 and is collected and detected by large area photosensor 136. A rotating shaft 137 has attached to it a plurality of chopper blades with two shown here; front blade 139 and rear blade 138. The blades are cut such that only one will block the beam at a time. From the time history of the eclipsing of the light by the chopper blades, one can quickly calculate the intensity profile. From the profiles as determined at the various chopper blade locations, one can estimate the focal point.

In an alternative embodiment, the chopper blades are replaced with one or more imaging areas which, through calculation, can also be used to determine the focal spot location.

INSTRUMENT CONFIGURATIONS

Figure 4A:
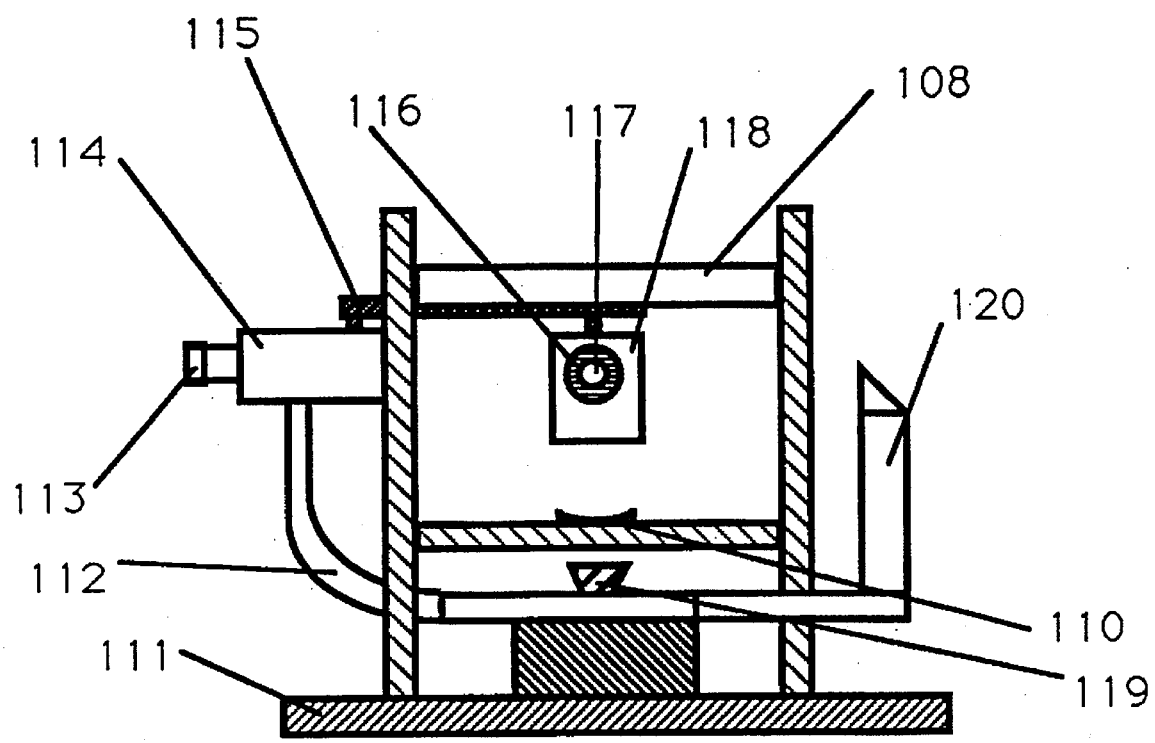
FIG. 4A is a front view of a tonometer mounted on a slit lamp.
Figure 4B:
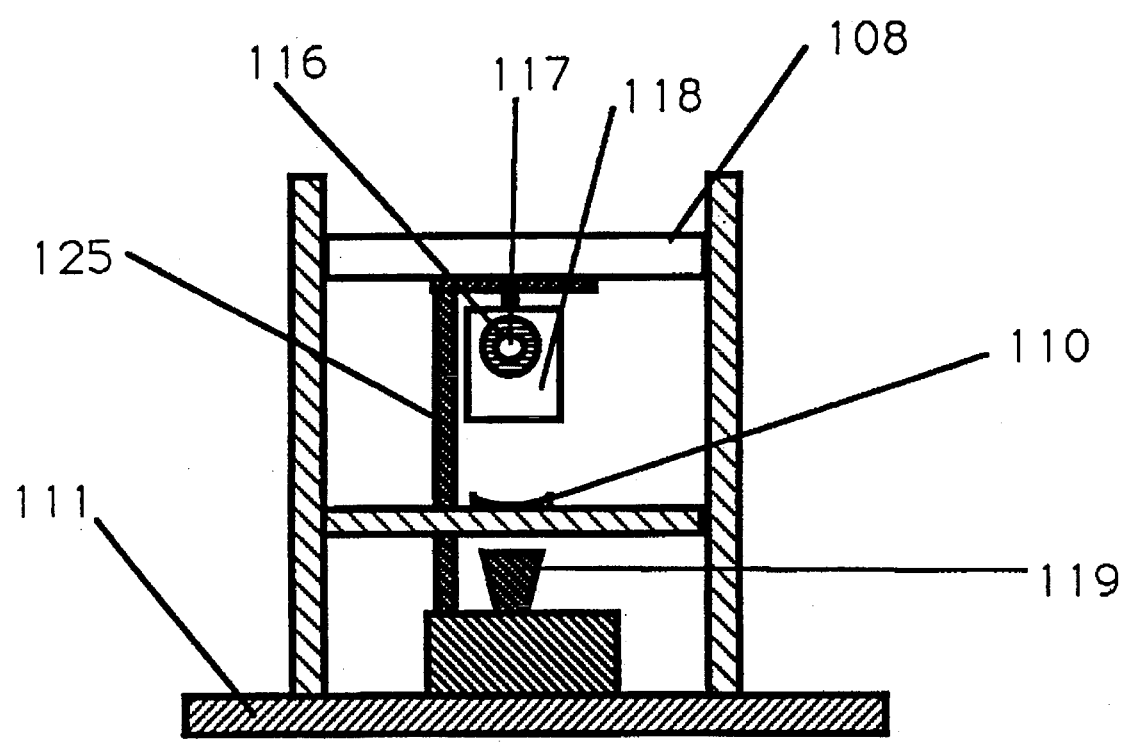
FIG. 4B is a front view of a tonometer constructed for home use.
Figure 4C:
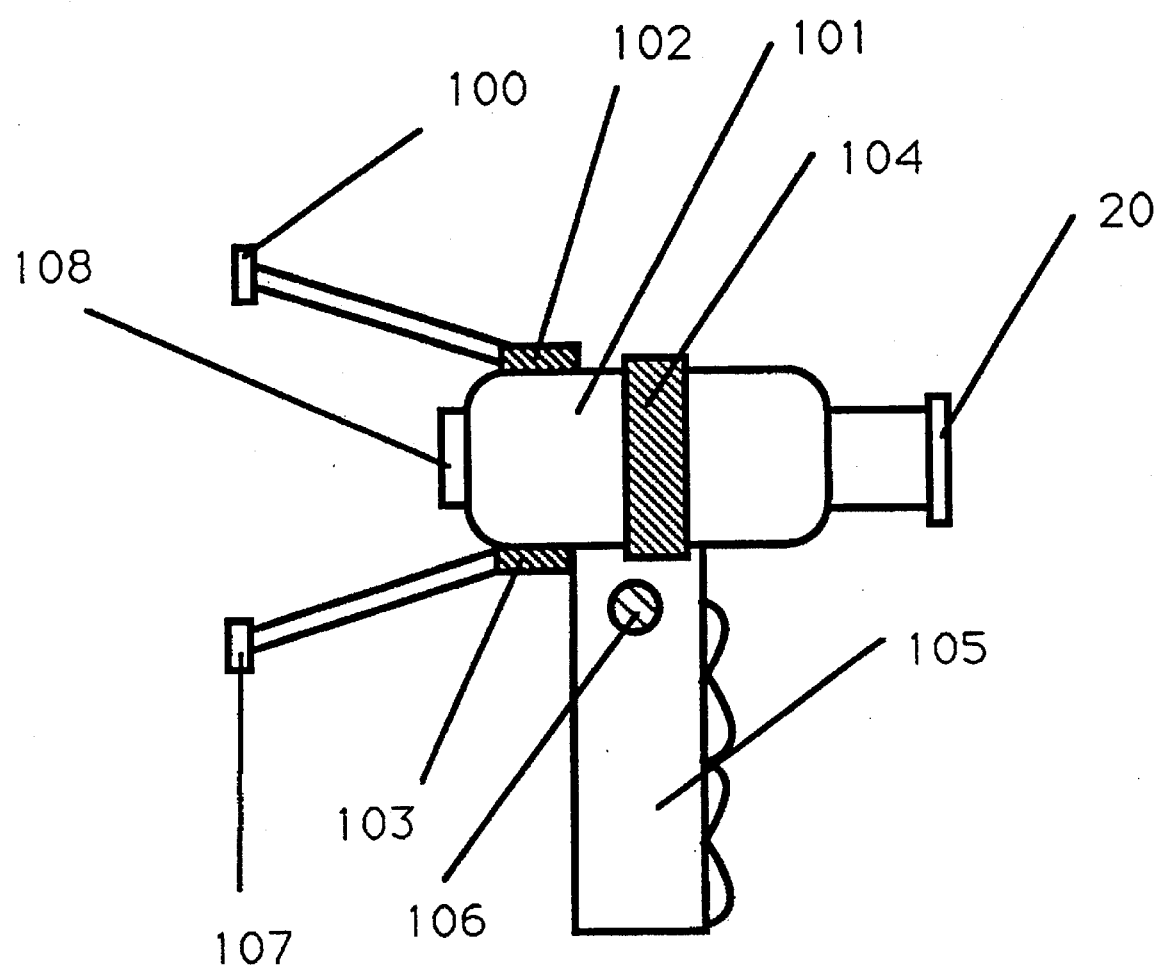
FIG. 4C is a side view of a tonometer designed for hand-held use.

The tonometer can be implemented in several different configurations; the four implementations which are most likely to be commercially significant are illustrated in FIGS. 4A, 4B and 4C. FIG. 4A shows the tonometer as it could be mounted on the common doctor's slit-lamp. A slit-lamp is actually a lamp which can project illumination onto the eye in a rectangular or slit-like area. The slit lamp stand also has a low power microscope mounted on it for examining the eye. The common Goldmann tonometer is frequently attached to the top of the microscope such that it can be swung to the side when not needed or in front of the microscope for use on the patient.

FIG. 4A shows the same mounting scheme as that used by the Goldmann tonometer. The base 111 of the apparatus has mounted onto it the patient head support system comprised of chin rest 110 and forehead rest 108, the slit lamp 120, and the microscope 114 with ocular 113 mounted on swing-out arm 112. The slit lamp 120, the microscope 114 and the tonometer 118 can be moved in the x, y, and z directions using a mechanical joystick 119 control mechanism. When not in use, the tonometer 118 swings out of the way by using swing-arm support 115 to the side of the microscope 114 for storage. Also shown are the tonometer ultrasound transducer 116 and objective lens 117.

FIG. 4B shows a simplified version, for example for home use. It would use a patient head support similar to that of a doctor's slit lamp which is comprised of table 111, chin rest 110, and forehead support strap 108 but the microscope 114 and slit lamp 120 are not provided. As described below, the patient can obtain alignment signals and, by using joystick 119, attached to the tonometer 118 through support 125, can adjust and align the tonometer to his or her own eye.

For home use of the tonometer as disclosed in FIG. 4B, it is necessary to provide the patient with alignment signals. The alignment system of FIG. 5A provides separate light sources for patient fixation and for sensing and alignment. The sources will be color coded. For persons who are color blind, the lights could be made to blink on/off in a sequential manner. For example, a first color could be on for a shod period, then a second color for a long period, followed by no lights for a short period.

The patient fixation light, being focused on the cornea, will make a small spot on the retina the size of which is not significantly affected by the patient's visual correction. The collimated sensing and alignment light will have a spot size that is affected by the patient's visual error. In this case, the spots may be differentiated by differing spot sizes.

To align the system in the x and y directions (orthogonal directions to the instrument's optical axis), the patient must use the joy-stick 119 to make the two light sources appear coincident. This accomplishes the same alignment procedure as that done by the doctor when overlaying the glint of the sensing and fixation beams (to be centered on the reticle). The instrument may be equipped with ultrasonic or other means for measuring the patient-to-instrument distance. The patient can be given additional aural clues as to whether this distance is too short or too long and these clues can guide the patient in adjusting the instrument for proper alignment. Once the instrument is aligned as determined by the instrument's own internal alignment checking mechanism, the patient can be given aural clues to remain stationary while the instrument obtains a set of IOP readings.

FIG. 4C shows a hand-held version of the tonometer. The tonometer is held in the pistol grip 105 and rested against the patient's forehead using footplate 100 and against the patient's cheek using footplate 107. The footplates 100, 107 are attached to the body 101 of the tonometer by swivels 102, 103 to allow for adjustment in both tip and tilt. The distance between the tonometer and the patient's eye is adjustable by means 104, possibly a coarse thread screw. The operator adjusts the positioning of the tonometer while visualizing the eye through ocular 20 as seen through objective lens 108. Once aligned, the system is triggered using button 106. Additionally, the tonometer may be mounted on the stand used by doctors in the operating room.

MEASURING OR ESTIMATING THE APPLIED PRESSURE

In order to estimate the IOP, as stated above, we need to be able to estimate the radiation pressure being applied so we can make a correlation of the pressure with the degree of deformation of the cornea. Persons skilled in this art will recognize that this can be done in several ways. In a well designed ultrasonic system, the ultrasonic radiation pressure is proportional to the square of the applied voltage. Thus, once the device has been built and calibrated, the ultrasonic radiation pressure can be determined by a voltmeter at the transducer or perhaps more simply be a knowledge of the digital work applied to an analog converter which will drive the high voltage amplifier driving the transducer. An alternate approach to determining the radiation pressure would be to measure it directly during the examination. One could place an acoustic beam splitter(a sheet of plastic for example) between the transducer and the eye and measure the acoustic levels of a sampled portion of the transducer output.

From the above description, it will be apparent that the invention disclosed herein provides a novel and advantageous apparatus for non-contact tonometry. The foregoing discussion discloses and describes merely exemplary methods and embodiments of the present invention. As will be understood by those familiar with the art, the invention may be embodied in other specific forms without departing from the spirit or essential characteristics thereof. Different configurations or specific parts may be used. Accordingly, the disclosure of the present invention is intended to be illustrative, but not limiting, of the scope of the invention, which is set forth in the following claims.

I claim:

1. A non-contact tonometer for measuring the intraocular pressure of an eye, the cornea of said eye having a generally convex surface, comprising:
   a) an ultrasonic transducer means configured to focus a beam of acoustic radiation on a spot on the surface of said cornea so to produce sufficient radiation pressure at said spot to temporally distort the surface of said cornea,
   b) a distortion detection means for detecting distortion caused by said radiation pressure,
   c) an acoustic radiation pressure estimating means for providing a signal from which the radiation pressure on said spot can be estimated,
   d) a means for correlating said signal with the distortion to estimate the intraocular pressure.

2. A non-contact tonometer as in claim 1 wherein said distortion detection means comprises a light source and a photosensor.

3. A non-contact tonometer as in claim 1 wherein said distortion detection means comprises a means for determining when a portion of the surface of said cornea within said spot is distorted into a plane.

4. A non-contact tonometer as in claim 3 wherein said signal is an electric voltage input to said ultrasonic transducer means.

5. A non-contact tonometer as in claim 4 wherein said correlating means comprises a means for determining a voltage input when said portion of the surface of said cornea within said spot is distorted into a plane.

6. A non-contact tonometer for measuring the intraocular pressure of an eye, the cornea of said eye having a generally convex surface, comprising:
   a) an ultrasonic transducer configured to focus a beam of acoustic radiation on a spot on the surface of said cornea so to produce sufficient radiation pressure at said spot to temporally distort the surface of said cornea,
   b) a light source and a photodetector arranged to detect light reflection from the surface of said cornea so as to determine when the surface of the cornea is distorted to a plane,
   c) an voltmeter configured to measure the voltage input to said ultrasonic transducer,
wherein, based on previously determined calibration data, said intraocular pressure may be determined by a measurement of the voltage input to said ultrasonic transducer at times when said cornea is distorted into a plane.

7. A method of measuring the intraocular pressure of an eye, the cornea of said eye having a generally convex surface, comprising the steps of:
   a) generating a beam of acoustic radiation and focusing said radiation on a spot on the surface of said cornea so to produce sufficient radiation pressure at said spot to distort the surface of said cornea at said spot from convex to planar to concave,
   b) directing a light source onto said spot and measuring the reflection of said source from said spot with a photodetector so as to determine as a function of time when the surface of the cornea is distorted to planar,
   c) measuring as a function of time a voltage input to said ultrasonic transducer,
   d) determining with the aid of calibration data said intraocular pressure utilizing the measured voltage input to said ultrasonic transducer when said cornea is distorted to planar.

8. A method of measuring the intraocular pressure of an eye, the cornea of said eye having a generally convex surface, comprising the steps of:
   a) generating with a transducer a beam of acoustic radiation fluctuating in intensity and focusing said fluctuating beam on a spot on the surface of said cornea so to produce sufficient radiation pressure at said spot to fluctuatingly distort the surface of said cornea at said spot into surfaces which are repeatedly convex, planar and concave,
   b) directing a light source onto said spot and measuring the reflection of said source from said spot with a photosensor so as to determine as a function of time when the surface of said cornea is distorted to planar,
   c) determining as a function of time a transducer signal indicative of radiation pressure produced by said transducer,
   d) determining, with the aid of calibration data, said intraocular pressure as a function of time utilizing values of said transducer signal determined when said cornea is distorted to planar.

9. A method of measuring the intraocular pressure of an eye, the cornea of said eye having a generally convex surface, comprising the steps of:
   a) generating with a first transducer a first beam of acoustic radiation fluctuating in intensity and focusing said fluctuating beam on a spot on the surface of said cornea so to produce sufficient radiation pressure at said spot to fluctuatingly distort the surface of said cornea at said spot into surfaces which are repeatedly convex, planar and concave,
   b) directing a second acoustic beam onto said spot and measuring the reflection of said second beam from said spot with an acoustic detector so as to determine as a function of time when the surface of said cornea is distorted to planar,
   c) determining as a function of time a transducer signal indicative of radiation pressure produced by said first transducer,
   d) determining, with the aid of calibration data, said intraocular pressure as a function of time utilizing values of said transducer signal determined when said cornea is distorted to planar.

10. A method of measuring the intraocular pressure of an eye, the cornea of said eye having a generally convex surface, comprising the steps of:
   a) generating a beam of acoustic radiation fluctuating in intensity and focusing said fluctuating beam on a spot on the surface of said cornea so to produce sufficient radiation pressure at said spot to fluctuatingly distort the surface of said cornea at said spot into surfaces which are repeatedly convex, planar and concave,
   b) directing a light source onto said spot and measuring the reflection of said source from said spot with a photosensor so as to determine as a function of time when the surface of said cornea is distorted planar,
   c) determining as a function of time a voltage input to said ultrasonic transducer,
   d) determining, with the aid of calibration data, said intraocular pressure as a function of time utilizing the determined voltage inputs to said ultrasonic transducer when said cornea is distorted to planar.

* * * * *